(12) United States Patent
Lee et al.

(10) Patent No.: US 8,729,230 B2
(45) Date of Patent: May 20, 2014

(54) PROTEINS ACTIVATING PRO-PHENOLOXIDASE SYSTEM AND GENES ENCODING THE SAME

(75) Inventors: Bok-Luel Lee, Busan (KR); Ji-Won Park, Busan (KR); Nam-Chul Ha, Busan (KR); Chan-Hee Kim, Busan (KR); Su-Jin Kim, Busan (KR); Kyung-Baeg Roh, Busan (KR)

(73) Assignee: Yhan Corporation, Seoul (KR)

( * ) Notice: Subject to any disclaimer, the term of this patent is extended or adjusted under 35 U.S.C. 154(b) by 650 days.

(21) Appl. No.: 12/526,482

(22) PCT Filed: Feb. 4, 2008

(86) PCT No.: PCT/KR2008/000664
§ 371 (c)(1),
(2), (4) Date: Aug. 7, 2009

(87) PCT Pub. No.: WO2008/096994
PCT Pub. Date: Aug. 14, 2008

(65) Prior Publication Data
US 2010/0317042 A1 Dec. 16, 2010

(30) Foreign Application Priority Data
Feb. 8, 2007 (KR) .................. 10-2007-0013231

(51) Int. Cl.
*C07K 14/00* (2006.01)

(52) U.S. Cl.
USPC ........................................... 530/350

(58) Field of Classification Search
None
See application file for complete search history.

(56) References Cited

U.S. PATENT DOCUMENTS

2006/0269982 A1 11/2006 Kovalenko et al.

FOREIGN PATENT DOCUMENTS

| WO | 02101083 A1 | 12/2002 |
|---|---|---|
| WO | 2004086039 A2 | 10/2004 |

OTHER PUBLICATIONS

Kim et al, A three-step proteolytic cascade mediates the activation of the peptidoglycan-induced toll pathway in an insect. J Biol Chem. Mar. 21, 2008;283(12):7599-607. Epub Jan. 14, 2008.*
Graham et al, Characterization and cloning of a Tenebrio molitor hemolymph protein with sequence similarity to insect odorant-binding proteins. Insect Biochem Mol Biol. Apr. 27, 2001;31(6-7):691-702.*
Supplementary European Search Report in corresponding EP Application No. 08 71 2316, dated Jun. 24, 2010, 11 pages.

Y. Kim et al.: "Gram-negative Bacteria-binding Protein, a Pattern Recognition Receptor for Lipopolysaccharide and β-1,3-Glucan That Mediates the Signaling for the Induction of Innate Immune Genes in *Drosophila melanogaster* Cells," Journal of Biological Chemistry, vol. 275, No. 42, Oct. 20, 2000, pp. 32721-32727.
Database UniProt [Online]: "SubName: Full=Gram-negative bacteria binding protein," Jul. 25, 2006, XP-002588645, 2 pages.
Database UniProt [Online]: "SubName: Full=Gram negative binding protein subgroup A (AGAP006761-PA)," Dec. 15, 2003, XP002588646, 2 pages.
J.W. Park et al.: "A synthetic peptidoglycan fragment as a competitive inhibitor of the melanization cascade," J. Biol. Chem., vol. 281, No. 12, pp. 7747-7755, 2006.
S. Li, et al.: "Bacteriolytic activity and specificity of *Achromobacter* beta-lytic protease," J. Biochem., vol. 124, No. 2, pp. 332-339, 1998.
S.R. Filipe, et al.: "Requirements of peptidoglycan structure that allow detection by the *Drosophila* Toll pathway," EMBO Rep., vol. 6, No. 4, pp. 327-333, 2005.
K. Ahmed, et al.: "Purification, bacteriolytic activity, and specificity of beta-lytic protease from *Lysobacter* sp. IB-9374," J. Biosci. Bioeng., vol. 95, No. 1, pp. 27-34, 2003.
R.S. Rosenthal, et al.: "Isolation of peptidoglycan and soluble peptidoglycan fragments," Methods Enzymol., vol. 235, pp. 253-285, 1994.
C.H. Kim, et al.: "A Three-step Proteolytic Cascade Mediates the Activation of the Peptidoglycan-induced Toll Pathway in an Insect," J. Biol. Chem., vol. 283, No. 12, pp. 7599-7607, 2008.
V. Bischoff, et al.: "Function of the *Drosophila* pattern-recognition receptor PGRP-SD in the detection of Gram-positive bacteria," Nat. Immunol., vol. 5, No. 11, pp. 1175-1180, 2004.
B. L. M. de Jonge, et al.: "Peptidoglycan Composition of a Highly Methicillin-resistant *Staphylococcus aureus* Strain: The Role of Penicillin Binding Protein 2A," J. Biol. Chem., vol. 267, No. 16, pp. 11248-11254, 1992.
L. Buck, et al.: "A Novel Multigene Family May Encode Odorant Receptors: A Molecular Basis for Odor Recognition," Cell, vol. 65, pp. 175-187, 1991.
L. Cerenius, et al.: "The prophenoloxidase-activating system in invertebrates," Immunol. Rev., vol. 198, pp. 116-126, 2004.
C. Chang, et al.: "Structure of Tracheal Cytotoxin in Complex with a Heterodimeric Pattern-Recognition Receptor," Science, vol. 311, pp. 1761-1764, 2006.
C. Chang, et al.: "Structure of the ectodomain of *Drosophila* peptidoglycan-recognition protein LCa suggests a molecular mechanism for pattern recognition," Proc. Natl. Acad. Sci., vol. 102, No. 29, pp. 10279-10284, 2005.

(Continued)

*Primary Examiner* — Sheridan Swope
(74) *Attorney, Agent, or Firm* — Rothwell, Figg, Ernst & Manbeck, P.C.

(57) ABSTRACT

The present invention provides novel proteins activating pro-phenoloxidase (pro-PO) system of *Tenebrio molitor*, genes encoding the same, methods of detecting bacterial infection in a sample using the proteins, and kits for detecting bacterial infection in a sample using the proteins. The present invention also provides a method of preparing a soluble linearized Lys-type pep-tidoglycan (SLPG), useful for a standard substance for the kit.

2 Claims, 18 Drawing Sheets

(56) References Cited

OTHER PUBLICATIONS

C. Chang, et al.: "A *Drosophila* Pattern Recognition Receptor Contains a Peptidoglycan Docking Groove and Unusual L,D-Carboxypeptidase Activity," PLoS Biol., vol. 2, No. 9, pp. 1293-1302, 2004.
K. Choe, et al.: "Requirement for a Peptidoglycan Recognition Protein (PGRP) in Relish Activation and Antibacterial Immune Responses in *Drosophila*," Science, vol. 296, pp. 359-362, 2002.
V. Gobert, et al.: "Dual Activation of the *Drosophila* Toll Pathway by Two Pattern Recognition Receptors," Science, vol. 302, pp. 2126-2130, 2003.
M. Gottar, "The *Drosophila* immune response against Gram-negative bacteria is mediated by a peptidoglycan recognition protein," Nature, vol. 416, pp. 640-644, 2002.
R. Guan, et al.: "Structural basis for peptidoglycan binding by peptidoglycan recognition proteins," Proc. Natl. Acad. Sci., vol. 101, No. 49, pp. 17168-17173, 2004.
C. Ji, et al. "A Pattern Recognition Serine Proteinase Triggers the Prophenoloxidase Activation Cascade in the Tobacco Hornworm, *Manduca sexta*," J. Biol. Chem., vol. 279, No. 33, pp. 34101-34106, 2004.
M. Kanost, et al.: "Innate immune responses of a lepidopteran insect, *Manduca sexta*," Immunol. Rev., vol. 198, pp. 97-105, 2004.
M. Kim, "Crystal structure of peptidoflycan recognition protein LB from *Drosophila melanogaster*," Nat. Immunol., vol. 4, No. 8, pp. 787-793, 2003.
N. Keep, et al.: "Wake up! Peptidoglycan lysis and bacterial non-growth states," Trends Microbiol., vol. 14, No. 6, pp. 271-276, 2006.
S. Krauss, et al.: "A Functionally Conserved Homolog of the *Drosophila* Segment Polarity Gene hh is Expressed in Tissues with Polarizing Activity in Zebrafish Embryos," Cell, vol. 75, pp. 1431-1444, 1993.
S. Li, et al.: "Purification, Staphylolytic Activity, and Cleavage Sites of α-Lytic Protease from *Achromobacter lyticus*," J. Biochem., vol. 122, No. 4, pp. 772-778, 1997.
J. Lim, et al.: "Structural Basis for Preferential Recognition of Diaminopimelic Acid-type Peptidoglycan by a Subset of Peptidoglycan Recognition Proteins," J. Biol. Chem., vol. 281, No. 12, pp. 8286-8295, 2006.

F. Leulier, et al.: "The *Drosophila* immune system detects bacteria through specific peptidoglycan recognition," Nat. Immunol., vol. 4, No. 5, pp. 478-484, 2003.
T. Michel, et al.: "*Drosophila* Toll is activated by Gram-positive bacteria through a circulating peptidoglycan recognition protein," Nature, vol. 414, pp. 756-759, 2001.
T. Muta, et al.: "Purified Horseshoe Crab Factor F," J. Biol. Chem., vol. 270, No. 2, pp. 892-897, 1995.
S. Pili-Floury, et al.: "In Vivo RNA Interference Analysis Reveals an Unexpected Role for GNBP1 in the Defense against Gram-positive Bacterial Infection in *Drosophila* Adults," J. Biol. Chem., vol. 279, No. 13, pp. 12848-12853, 2004.
R. Riddle, et al.: "Sonic hedgehog Mediates the Polarizing Activity of the ZPA," Cell, vol. 75, pp. 1401-1416, 1993.
K. Schleifer, et al.: "Peptidoglycan Types of Bacterial Cell Walls and their Taxonomic Implications," Bacteriol. Rev., vol. 36, No. 4, pp. 407-477, 1972.
K. Soderhall, et al.: "Activation of serum prophenoloxidase in arthropod immunity. The specificity of cell wall glucan activation and activation by purified fungal glycoproteins of crayfish phenoloxidase," Can. J. Microbiol. vol. 25, pp. 406-414, 1979.
A. Takehana, et al.: "Overexpression of a pattern-recognition receptor, peptidoglycan-recognition protein-LE, activates imd/relish-mediated antibacterial defense and the prophenoloxidase cascade in *Drosophila* larvae," Proc. Natl. Acad. Sci., vol. 99, No. 21, pp. 13705-13710, 2002.
L. Wang, et al.: "Sensing of Gram-positive bacteria in *Drosophila*: GNBP1 is needed to process and present peptidoglycan to PGRP-SA," EMBO J., vol. 25, No. 20, pp. 5005-5014, 2006.
Y. Wang, et al.: "Interaction of β-1, 3-Glucan with Its Recognition Protein Activates Hemolymph Proteinase 14, an Initiation Enzyme of the Prophenoloxidase Activation System in *Manduca sexta*," J. Biol. Chem., vol. 281, No. 14, pp. 9271-9278, 2006.
R. Zhang, et al.: "Characterization and Properties of a 1,3-β-D-Glucan Pattern Recognition Protein of *Tenebrio molitor* Larvae That Is Specifically Degraded by Serine Protease during Prophenoloxidase Activation," J. Biol. Chem., vol. 278, No. 43, pp. 42072-42079, 2003.

\* cited by examiner

FIG. 3
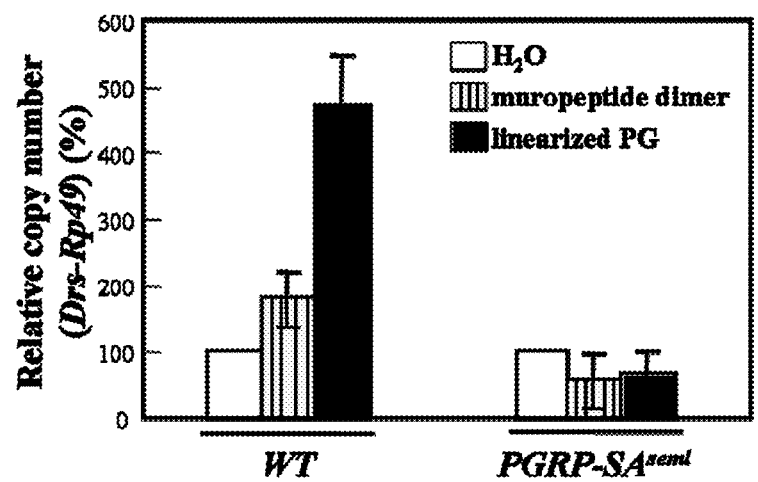
FIG. 4
(a)                        (b)
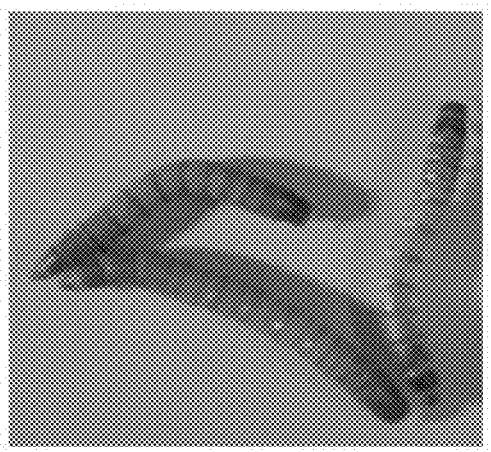 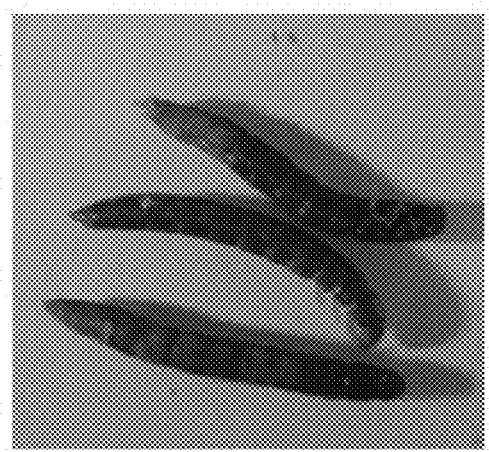

FIG. 9
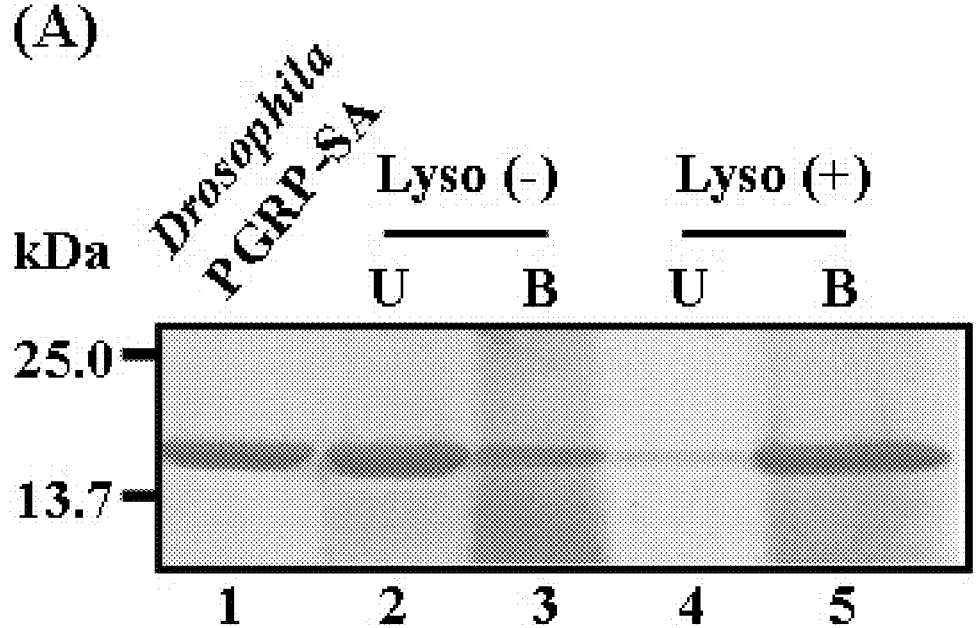
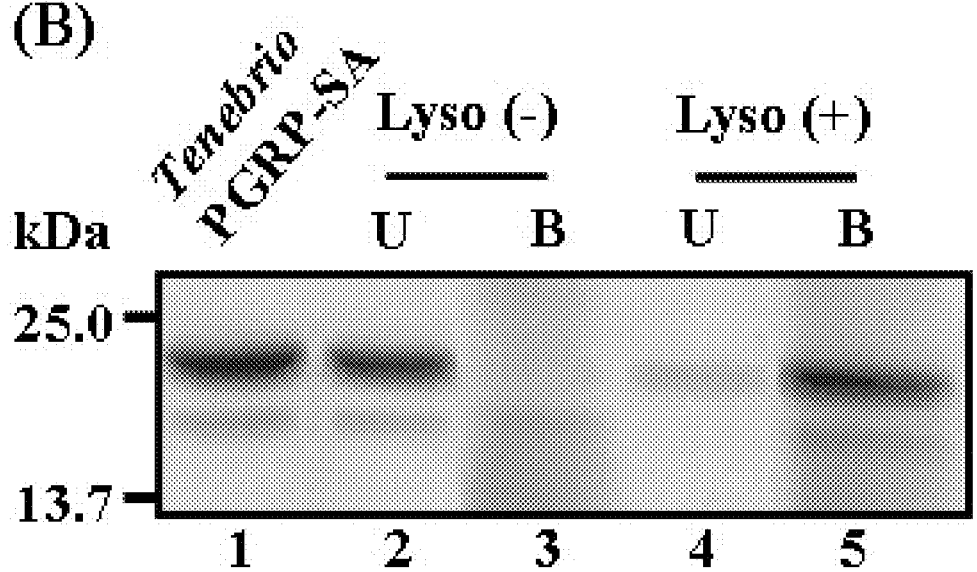

FIG. 10

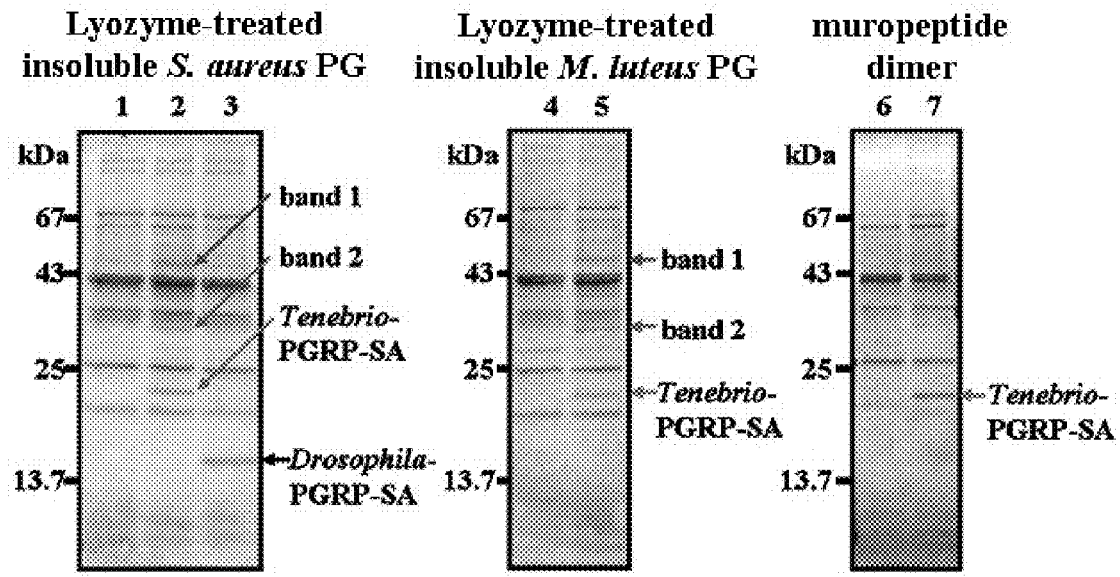

FIG. 11

(A)
```
band 1     1 EFVIPEVTLE AYEPKGFRAS IPALNGIQMF 30
Tc-GNBP   21 QFVIPDVTLE AYAPKGFRAS IPALPGIQMF 50
Tm-GRP    18 QFEVPDALVE VFRPRGLRVS IPDQEGIKLF 47
Ag-GNBP1  17 AYTIPAVRFE YPTMRGFRAS IPDTPGLQMF 46
Dm-GNBP1  19 AYKIPTPTVE LLET-GFSVS IPDEEGVKVV 47
```

(B)
```
band 2     1 IVNGKPVKKG DYPWQQALYT 20
Tc-SP    369 IVNGKTAKRG TYPWQAALYT 388
Ms-HP14  405 VLGGERAQFG ELPWQAGIYT 424
Ag-SP    336 IIGGRNVSIA EVPWHMAIYK 355
Dm-SP    375 INNT-VV--- --PWHVGLYV 388
```

(C)
```
Peak 1     1 DNSDEIRATCWNVRCPGFTHK 21
Tc-SP    149 DRSDEIRATCWNLRCPIYSYK 170

Peak 2     2 YGACINIALECDPK 14
Tc-SP     86 YGACISADLECDGK 99
```

FIG. 13
(A) *Tenebrio* PGRP-SA
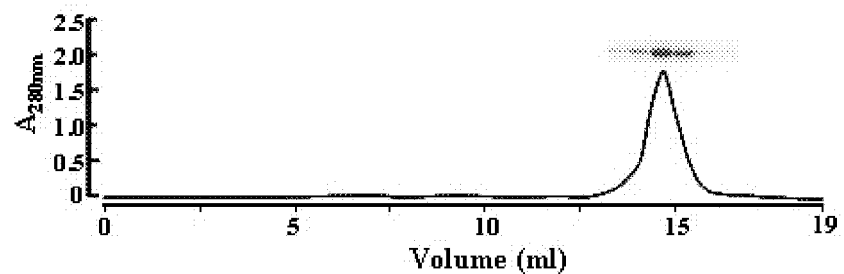
(B) *Tenebrio* PGRP-SA + linearized PG
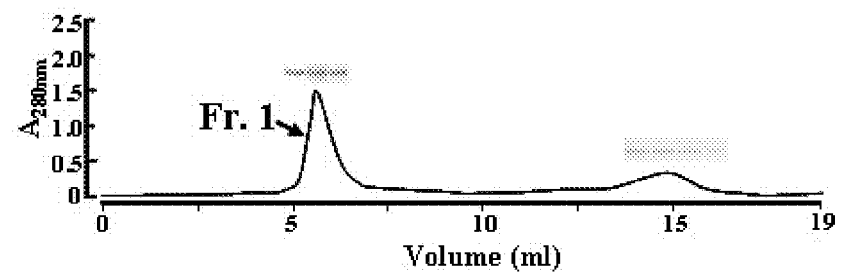
(C) *Drosophila* PGRP-SA + linearized PG
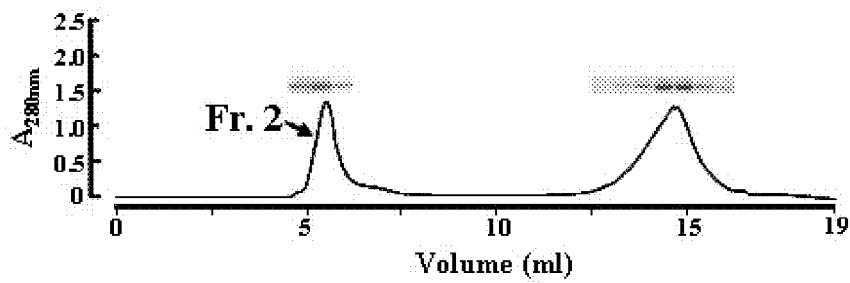
(D) *Tenebrio* PGRP-SA + muropeptide dimer
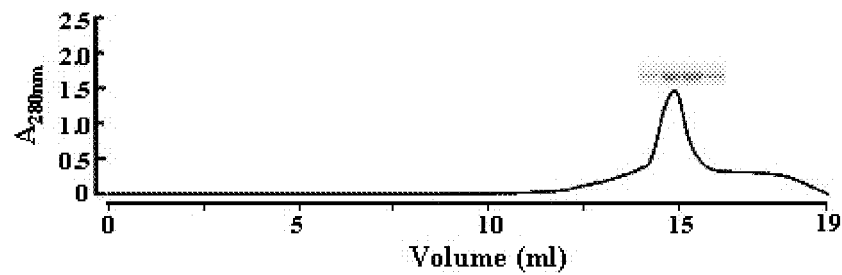

FIG. 15

```
         10        20        30        40        50        60
ATGTTTGCTAAAGCAATAATATTGTTTCTTATATTAACCACTTTCCAATGTCATGGAGAA
 M  F  A  K  A  I  I  L  F  L  I  L  T  T  F  Q  C  H  G  E 70        80        90       100       110       120
TTTGTTATACCGGAAGTGACGTTAGAAGCGTACGAACCGAAAGGGTTTAGAGCATCAATT
 F  V  I  P  E  V  T  L  E  A  Y  E  P  K  G  F  R  A  S  I 130       140       150       160       170       180
CCAGCCTTAAATGGAATACAGATGTTTGCTTTTCATGGGAATATAAACAAACCAATATCG
 P  A  L  N  G  I  Q  M  F  A  F  H  G  N  I  N  K  P  I  S 190       200       210       220       230       240
CAGGTTGATCCTGGAGAGTACAGTCAAGATTATACTTCTCCAACTGGTAATACGTGGTCT
 Q  V  D  P  G  E  Y  S  Q  D  Y  T  S  P  T  G  N  T  W  S 250       260       270       280       290       300
TATTTTAACAAAGACTTGAAGCTAAAAGCCGGGGATGTAATTCATTACTGGGTATTTATC
 Y  F  N  K  D  L  K  L  K  A  G  D  V  I  H  Y  W  V  F  I 310       320       330       340       350       360
CAATTTTTAAAATTAGGATATAGAAAAGACAATCAAGTGTGGAACGTAACAGAACTGGTG
 Q  F  L  K  L  G  Y  R  K  D  N  Q  V  W  N  V  T  E  L  V 370       380       390       400       410       420
CAGTTAAAAAACTCATCCTGTGAGACAAGTCCTACAACAGTTAGAGGAAGATCTGTGATT
 Q  L  K  N  S  S  C  E  T  S  P  T  T  V  R  G  R  S  V  I 430       440       450       460       470       480
TGTAAAAATAGCATTATTTTTGAAGAAAATTTCAACGGGGAAGGAATTGACACCAAGAAA
 C  K  N  S  I  I  F  E  E  N  F  N  G  E  G  I  D  T  K  K 490       500       510       520       530       540
TGGCTTATCGAACAATATATTCCCACGTATACCAGCCTGGATTATGAATTTGTTTCTTAT
 W  L  I  E  Q  Y  I  P  T  Y  T  S  L  D  Y  E  F  V  S  Y 550       560       570       580       590       600
CAAAATGACCCAACTGTATGTTTTTTAAATGACAATAAACTATTTATAAAACCAAAATAT
 Q  N  D  P  T  V  C  F  L  N  D  N  K  L  F  I  K  P  K  Y
```

FIG. 16

```
           610        620        630        640        650        660
    GCACAAAGTGAAGCCGAAGTAAATGGTGAACTAGATTTTAGAAACAGATGTACTAGGAAA
     A  Q  S  E  A  E  V  N  G  E  L  D  F  R  N  R  C  T  R  K 670        680        690        700        710        720
    ACAGATGAAGAATGTTATAAAAAACGAGAAATTTATTTCATAATTCCACCTGTGACTTCT
     T  D  E  E  C  Y  K  R  E  I  Y  F  I  I  P  P  V  T  S 730        740        750        760        770        780
    GGAAGACTTGTTTCTGATTTTCGATTTAAATATGGTAAAGTTGAAATTAGGGCGAAGTTA
     G  R  L  V  S  D  F  R  F  K  Y  G  K  V  E  I  R  A  K  L 790        800        810        820        830        840
    CCTGCAGGGGACTGGATATATCCACAAATGTACTTAGAACAAGTAAATGATCCAAAAAG
     P  A  G  D  W  I  Y  P  Q  M  Y  L  E  Q  V  N  D  P  K  K 850        860        870        880        890        900
    AAAATATGGATTGGTTATGCCAGAGGAAATAATAAATTACTGGCAAATAATCAGGAAGAC
     K  I  W  I  G  Y  A  R  G  N  N  K  L  L  A  N  N  Q  E  D 910        920        930        940        950        960
    ATTGGAGGCAATTTACTTTTTGGTGGACCTGTTTTAGATCCAGAAGAACCTCATAGAAGT
     I  G  G  N  L  L  F  G  G  P  V  L  D  P  E  E  P  H  R  S 970        980        990       1000       1010       1020
    CAATATTTGAAAAGTACTCGGAACAGCAAACCTTTTACAAGTCAAATGCACACTCTTGTT
     Q  Y  L  K  S  T  R  N  S  K  P  F  T  S  Q  M  H  T  L  V 1030       1040       1050       1060       1070       1080
    GTACTTTGGGATGAAGATCACATTTCGTTACAATTAAATGGTATTGAATATGGCAAGATC
     V  L  W  D  E  D  H  I  S  L  Q  L  N  G  I  E  Y  G  K  I 1090       1100       1110       1120       1130       1140
    GATAAAAGGACAATGCAAGAAGTAAACTTTGCAGATAACGATATGGTCCGCTTAGTTCTT
     D  K  R  T  M  Q  E  V  N  F  A  D  N  D  M  V  R  L  V  L 1150       1160       1170       1180       1190       1200
    GGAGTAGGGGTGGGAGGAGTCAATGATTTTCCCAGATGATTTTCCGATCAGGAACTAACGTA
     G  V  G  V  G  G  V  N  D  F  P  D  D  F  R  S  G  T  N  V
```

FIG. 17

```
        1210       1220       1230       1240       1250       1260
AAACCTTGGCGCAACAAAGACAATAAACAAGTTAAAAATTTCTTTACGGCAAGAAGTGAA
  K  P  W  R  N  K  D  N  K  Q  V  K  N  F  F  T  A  R  S  E 1270       1280       1290       1300       1310       1320
TGGGGGAAAACTTGGAGCGGTGACAATTGTGCTTTACAGGTTGATTATATTAAAGTGTGG
  W  G  K  T  W  S  G  D  N  C  A  L  Q  V  D  Y  I  K  V  W

1330
GCTTTATAG
  A  L  *
```

FIG. 18

```
          10        20        30        40        50        60
ATGTGCAATGTAAGAACATTACTGCAGGTGATTTGTTTAAGTCTTATTGTTATACAGACA
 M  C  N  V  R  T  L  L  Q  V  I  C  L  S  L  I  V  I  Q  T 70        80        90       100       110       120
                                                  CCA
GTCGATAGCTACAGTTTTGCACTAAGCAAATTTACGAGAATTCGACGCCAAGCCCGACGA
 V  D  S  Y  S  F  A  L  S  K  F  T  R  I  R  R  Q  A  R  R
                                                  P 130       140       150       160       170       180
ACCTGTACAAGTACTGAGTTTGCTTGCAAATCCGGAGAATGCATCGACGAAGATAAAGAG
 T  C  T  S  T  E  F  A  C  K  S  G  E  C  I  D  E  D  K  E 190       200       210       220       230       240
            GTA
TGTGACGGTATTGTGGACTGTACAGATGCCAGCGACGAGACCAACGCCTGTCACAGGATC
 C  D  G  I  V  D  C  T  D  A  S  D  E  T  N  A  C  H  R  I 250       260       270       280       290       300
AAATGCCCCAATTATCTGTTCCGGTGCAAATATGGCGCTTGCATCAATCCGGACCTGGAG
 K  C  P  N  Y  L  F  R  C  K  Y  G  A  C  I  N  P  D  L  E 310       320       330       340       350       360
                                                  GCG
TGCGACGGCAAACCGGACTGCATGGACGGATCCGACGAGAAAACGTCGAAATGTAAACCC
 C  D  G  K  P  D  C  M  D  G  S  D  E  K  T  S  K  C  K  P
                                                  A 370       380       390       400       410       420
GACGATTCGTCCCCGGAGTGCAAAGCGAACGAGTTTCGGTGCAGCTCCGGTCAGTGCATC
 D  D  S  S  P  E  C  K  A  N  E  F  R  C  S  S  G  Q  C  I 430       440       450       460       470       480
            TAC       TGC
CCGGAGGACTTCAAATGTGACGGCAAAGCCGAGTGCAAGGATAACTCCGACGAGATTAGA
 P  E  D  F  K  C  D  G  K  A  E  C  K  D  N  S  D  E  I  R
            Y
```

FIG. 19

```
         490       500       510       520       530       540
     GCCACCTGCTGGAACGTCCGCTGTCCAGGATTCACGCACAAGTGCAAATACGGAGCTTGC
      A  T  C  W  N  V  R  C  P  G  F  T  H  K  C  K  Y  G  A  C 550       560       570       580       590       600
     GTGAGCGGTAACGCCGAGTGCAACGGAATCGTCGAGTGTTTCGACGGTTCAGACGAAGAT
      V  S  G  N  A  E  C  N  G  I  V  E  C  F  D  G  S  D  E  D 610       620       630       640       650       660
                   AAG  GAA       AAA
     CCGGCGATTTGCAAAACTAAACCGACACCAAGGCGGACGCCGACTCCAGGAAGTCCCGGC
      P  A  I  C  K  T  K  P  T  P  R  P  T  P  T  P  G  T  P  G
                         E              K 670       680       690       700       710       720
     CCGCAACCGACACAGGGTGGCTGCGTCTTGCCGAATCATCCCGAATTTGGTGAGTGGCAA
      P  Q  P  T  Q  G  G  C  V  L  P  N  H  P  E  F  G  E  W  Q 730       740       750       760       770       780
                                        GCG
     GTGTACGGAATTCCTGGACAATTCTCTCCAGGAATGGTGATTAGAGCTGGTGCAACTTTG
      V  Y  G  I  P  G  Q  F  S  P  G  M  V  I  R  A  G  A  T  L
                                           A 790       800       810       820       830       840
     CGAATACAGTGCAAGAAACGTTACAAACTCGAAGGAAAAAACGCCATCTTTTGCGAAAAT
      R  I  Q  C  K  K  R  Y  K  L  E  G  K  N  A  I  F  C  E  N 850       860       870       880       890       900
     GGGAAGTGGTCGGATGCAGTCGGTCATTGCTTAAAGTTGTGCCCTTCCATCCAAAGTACT
      G  K  W  S  D  A  V  G  H  C  L  K  L  C  P  S  I  Q  S  T 910       920       930       940       950       960
     TCAACAATGAGGGTTACTTGTATTTATAACAAACACGAAGAGACTGAAAACTGCACAGAA
      S  T  M  R  V  T  C  I  Y  N  K  H  E  E  T  E  N  C  T  E
```

FIG. 20

```
          970       980       990      1000      1010      1020
GCTGTTGAGGGTACTCTTGTGAGGTTTGATTGCGCACCGTTTTATGAAGATTTGGGATTG
 A   V   E   G   T   L   V   R   F   D   C   A   P   F   Y   E   D   L   G   L 1030      1040      1050      1060      1070      1080
TCGAGACATCCTATTCATATCTGCCGAGATGGTTCCTGGGACCAGAGGAGACCAGAATGT
 S   R   H   P   I   H   I   C   R   D   G   S   W   D   Q   R   R   P   E   C 1090      1100      1110      1120      1130      1140
ACACCAGTGTGTGGGCAAAAGTCAGTTAACGCTCAAACATTAATTGTCAACGGGAAACCC
 T   P   V   C   G   Q   K   S   V   N   A   Q   T   L   I   V   N   G   K   P 1150      1160      1170      1180      1190      1200
                                    CCA
GTGAAGAAAGGAGATTATCCGTGGCAAGTCGCGTTATACACTTTGAACGATAAAGAGTTG
 V   K   K   G   D   Y   P   W   Q   V   A   L   Y   T   L   N   D   K   E   L 1210      1220      1230      1240      1250      1260
ATCTGTGGAGGATCCCTCTTAAACCAGCGAGTCGTTCTGACAGCTGCGCATTGTATAACT
 I   C   G   G   S   L   L   N   Q   R   V   V   L   T   A   A   H   C   I   T 1270      1280      1290      1300      1310      1320
GACGATAAGGGAAAATTGTTATCAAAGGAAAATTATATGGTGGCTGTGGGAAAGTACTAC
 D   D   K   G   K   L   L   S   K   E   N   Y   M   V   A   V   G   K   Y   Y 1330      1340      1350      1360      1370      1380
                                    TCC
CGACCATTCAATGACTCTCGAGACGGCAACGAAGCGCAGTTTTCTGAGGTAAAACACATG
 R   P   F   N   D   S   R   D   R   N   E   A   Q   F   S   E   V   K   H   M 1390      1400      1410      1420      1430      1440
         CCA
TTTATTCCCGAACTGTACAAGGGTTCCACACAAAACTACGTCGGAGATATCGCTATCTTG
 F   I   P   E   L   Y   K   G   S   T   Q   N   Y   V   G   D   I   A   I   L
```

FIG. 21

```
         1450       1460       1470       1480       1490       1500
GTAACACGAGTCACTTTCACCCTTTCCAGGAGAGTTCAGCCGGTGTGCATCGACTACGGT
 V  T  R  V  F  T  L  S  R  R  V  Q  P  V  C  I  D  Y  G 1510       1520       1530       1540       1550       1560
TTAAAATACACCTCTTATACAAACGAATTTGGATACGTTACGGGTTGGGGTTACACTCTG
 L  K  Y  T  S  Y  T  N  E  F  G  Y  V  T  G  W  G  Y  T  L 1570       1580       1590       1600       1610       1620
CAAAATGACAAACCTTCCGACGTGCTCAAAGAATTGAAAGTTGCAGCAGTTAGTACAGAA
 Q  N  D  K  P  S  D  V  L  K  E  L  K  V  P  A  V  S  T  E 1630       1640       1650       1660       1670       1680
                    ATA
CAATGTAGTAGCGCTATTCCTGAAGATTATGACATCTACCTTACACACGATAAACTGTGC
 Q  C  S  S  A  I  P  E  D  Y  D  I  Y  L  T  H  D  K  L  C 1690       1700       1710       1720       1730       1740
GCT
GCCGGCTATTTAGACAATGGTACTTCCGTGTGTAGCGGAGACAGTGGTGGAGGTTTGGTG
 A  G  Y  L  D  N  G  T  S  V  C  S  G  D  S  G  G  G  L  V 1750       1760       1770       1780       1790       1800
TTTAAATTTGATGGCAGGTACTACGTTACTGGGATTGTGAGTCTTTCTCCACAAGCATCA
 F  K  F  D  G  R  Y  Y  V  T  G  I  V  S  L  S  P  Q  A  S 1810       1820       1830       1840       1850       1860
ACAGGCGGCTGTGATACTCAACAATATGGTCTTTATACAAAGGTTGGCACCTACATTTCG
 T  G  G  C  D  T  Q  Q  Y  G  L  Y  T  K  V  G  T  Y  I  S 1870       1880       1890       1900
GATTTTATTATCAAAACGGAATCGCAGTTTAGGCCATAA
 D  F  I  I  K  T  E  S  Q  F  R  P  *
```

PROTEINS ACTIVATING PRO-PHENOLOXIDASE SYSTEM AND GENES ENCODING THE SAME

CROSS REFERENCE TO RELATED APPLICATIONS

This application is a 35 U.S.C. §371 National Phase Entry Application from PCT/KR2008/000664, filed Feb. 4, 2008, and designating the United States, which claims priority under 35 U.S.C. §119 to Korean Patent Application No. 10-2007-0013231 filed Feb. 8, 2007, which incorporated herein in entirety.

BACKGROUND OF THE INVENTION

1. Field of the Invention

The present invention relates to novel proteins activating pro-phenoloxidase (pro-PO) system of *Tenebrio molitor*, genes encoding the same, methods of detecting bacterial infection in a sample using the proteins, and kits for detecting bacterial infection in a sample using the proteins. The present invention also relates to a method of preparing a soluble linearized Lys-type peptidoglycan (SLPG), useful for a standard substance for the kit.

2. Description of Related Art

Recent genetic studies revealed that *Drosophila melanogaster* peptidoglycan (PG) recognition protein *Drosophila* PGRP-SA and *Drosophila* PGRP-SD activate the Toll pathway (Michel, T., Reichhart, J. M., Hoffmann, J. A. & Royet, J. (2001) *Nature* 414, 756-759; and Bischoff, V., Vignal, C., Boneca, I. G., Michel, T., Hoffmann, J. A. & Royet, J. (2004) *Nat Immunol* 5, 1175-1180), while *Drosophila* PGRP-LC and *Drosophila* PGRP-LE are receptors for the Imd pathway (Gottar, M., Gobert, V., Michel, T., Belvin, M., Duyk, G., Hoffmann, J. A., Ferrandon, D. & Royet, J. (2002) *Nature* 416, 640-644; Choe, K. M., Werner, T., Stoven, S., Hultmark, D. & Anderson, K. V. (2002) *Science* 296, 359-362; and Takehana, A., Katsuyama, T., Yano, T., Oshima, Y., Takada, H., Aigaki, T. & Kurata, S. (2002) *Proc Natl Acad Sci USA* 99, 13705-13710). The immune phenotype of a loss-of-function mutant of *Drosophila* Gram-negative bacteria binding protein 1 (*Drosophila* GNBP1) was indistinguishable from that of *Drosophila* PGRP-SA, demonstrating that these two proteins are required to activate the Toll pathway in response to Gram-positive bacterial infection (Gobert, V., Gottar, M., Matskevich, A. A., Rutschmann, S., Royet, J., Belvin, M., Hoffmann, J. A. & Ferrandon, D. (2003) *Science* 302, 2126-2130; Pili-Floury, S., Leulier, F., Takahashi, K., Saigo, K., Samain, E., Ueda, R. & Lemaitre, B. (2004) *J Biol Chem* 279, 12848-12853; and Wang, L., Weber, A. N., Atilano, M. L., Filipe, S. R., Gay, N. J. & Ligoxygakis, P. (2006) *EMBO J* 25, 5005-5014). However, the molecular mechanisms of the upstream part of the Toll pathway in Gram-negative bacteria recognition still remain to be elucidated.

The pro-phenoloxidase (pro-PO) activation cascade, which leads to melanization of invading microbes, is another major innate immune defense mechanism in invertebrates that is triggered by peptidoglycan (PG) and β-1,3-glucan (Cerenius, L. & Soderhall, K. (2004) *Immunol Rev* 198, 116-126; and Kanost, M. R., Jiang, H. & Yu, X. Q. (2004) *Immunol Rev* 198, 97-105). The pro-PO cascade, like the vertebrate complement system, is a proteolytic cascade in blood plasma. Therefore, the pro-PO system is an ideal tool for biochemical studies of PG and β-1,3-glucan recognition and subsequent signaling under a cell-free condition. We previously identified the *Tenebrio molitor* PGRP that exhibited the highest sequence homology with *Drosophila* PGRP-SA. This PGRP, which we designate *Tenebrio* PGRP-SA, activated the Lys-PG-dependent pro-PO system in *Tenebrio* beetle. Remarkably, a novel synthetic Lys-PG fragment functions as a competitive inhibitor of soluble polymeric linear Lys-PG in the activation of the pro-PO system. The synthetic Lys-PG fragment (hereinafter referred to as "synthetic muropeptide dimmer"), having a chemical structure of the following formula (I), is composed of tetra-saccharide (GlcNAc-MurNAc-GlcNAc-MurNAc), covalently linked to two copies of a tetrapeptide stem [L-Ala-D-isoGln-L-Lys-D-Ala] (Park, J. W., Je, B. R., Piao, S., Inamura, S., Fujimoto, Y., Fukase, K., Kusumoto, S., Soderhall, K., Ha, N. C. & Lee, B. L. (2006) *J Biol Chem* 281, 7747-7755).

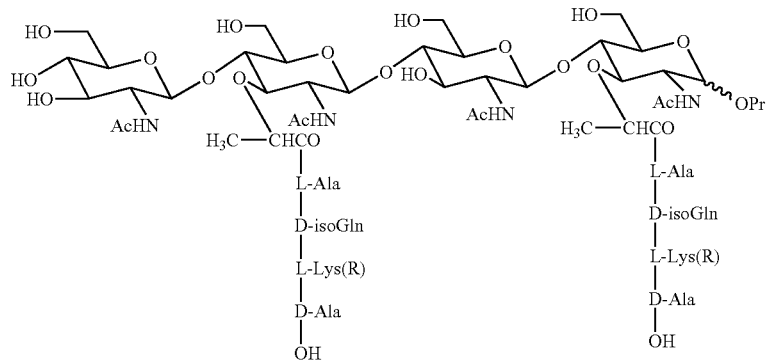

Chemical Formula 1

Recent crystallographic structural studies of PGRP proteins without PG-fragment or in complex with PG-fragments provided important insights into the structural basis for PG recognition (Lim, J. H., Kim, M. S., Kim, H. E., Yano, T., Oshima, Y., Aggarwal, K., Goldman, W. E., Silverman, N., Kurata, S. & Oh, B. H. (2006) *J Biol Chem* 281, 8286-8295; Chang, C. I., Chelliah, Y., Borek, D., Mengin-Lecreulx, D. & Deisenhofer, J. (2006) *Science* 311, 1761-1764; Chang, C. I., Ihara, K., Chelliah, Y., Mengin-Lecreulx, D., Wakatsuki, S. & Deisenhofer, J. (2005) *Proc Natl Acad Sci USA* 102, 10279-10284; Guan, R., Roychowdhury, A., Ember, B., Kumar, S., Boons, G. J. & Mariuzza, R. A. (2004) *Proc Natl Acad Sci USA* 101, 17168-17173; Kim, M. S., Byun, M. & Oh, B. H. (2003) *Nat Immunol* 4, 787-793; and Chang, C. I., Pili-Floury, S., Herve, M., Parquet, C., Chelliah, Y., Lemaitre, B., Mengin-Lecreulx, D. & Deisenhofer, J. (2004) *PLoS Biol* 2, E277). Muropeptide, composed of N-acetylglucosamine and N-acetylmuramic acid sugars linked with a short peptide chain as a stem, was revealed as the minimum binding unit for PGRP-SA.

However, it remains unclear how recognition signal of Lys-PG by PGRPs primes the serine protease (SP) cascade leading to activation of the pro-PO or Toll pathways.

BRIEF SUMMARY OF THE INVENTION

According to an aspect of the present invention, there are provided a *Tenebrio molitor*-derived Gram negative bacteria binding protein 1 (*Tenebrio* GNBP1), which has an amino acid sequence as set forth in SEQ ID NO: 2 and a polynucleotide encoding the same, e.g., a polynucleotide having a nucleotide sequence as set forth in SEQ ID NO: 3.

According to another aspect of the present invention, there are provided a *Tenebrio molitor*-derived modular serine protease-1 (*Tenebrio* MSP-1), which has an amino acid sequence as set forth in SEQ ID NO: 4 and a polynucleotide encoding the same, e.g., a polynucleotide having a nucleotide sequence as set forth in SEQ ID NO: 5.

According to still another aspect of the present invention, there are provided a molitor-derived modular serine protease-2 (*Tenebrio* MSP-2), which has an amino acid sequence as set forth in SEQ ID NO: 6 and a polynucleotide encoding the same, e.g., a polynucleotide having a nucleotide sequence as set forth in SEQ ID NO: 7.

According to still another aspect of the present invention, there is provided a method of detecting bacterial infection in a sample, the method comprising: (a) loading a *Tenebrio molitor*-derived peptidoglycan recognition protein (*Tenebrio* PGRP-SA) is having an amino acid sequence as set forth in SEQ ID NO: 1 to a sample and then performing an incubation thereof; (b) loading at least one protein selected from the group consisting of a *Tenebrio* GNBP1 having an amino acid sequence as set forth in SEQ ID NO: 2, a *Tenebrio* MSP-1 having an amino acid sequence as set forth in SEQ ID NO: 4, and *Tenebrio* MSP-2 having an amino acid sequence as set forth in SEQ ID NO: 6 to the incubation mixture of step (a) and then performing an incubation; and (c) detecting a reactivity between the protein and the sample in the incubation mixture of step (b).

According to still another aspect of the present invention, there is provided a kit for detecting bacterial infection in a sample comprising: a *Tenebrio* PGRP-SA having an amino acid sequence as set forth in SEQ ID NO: 1, and at least one protein selected from the group consisting of a *Tenebrio* GNBP1 having an amino acid sequence as set forth in SEQ ID NO: 2, a *Tenebrio* MSP-1 having an amino acid sequence as set forth in SEQ ID NO: 4, and *Tenebrio* MSP-2 having an amino acid sequence as set forth in SEQ ID NO: 6.

According to still another aspect of the present invention, there is provided a method of preparing a soluble linearized Lys-type peptidoglycan (SLPG), the method comprising: (a') suspending an insoluble peptidoglycan isolated from a bacteria in a buffer solution of about pH 8; (b') treating the suspension obtained from step (a') with β-lytic protease (blp); (c') heating the reaction mixture obtained from step (b') at about 95° C. for about 10 minutes, centrifuging the reaction mixture, and then collecting a supernatant; and (d') fractionizing the supernatant obtained from step (c') using a size-exclusion column to collect a fraction showing phenoloxidase (PO) activity.

BRIEF DESCRIPTION OF THE DRAWINGS

FIG. 3 shows induction of the drosomycin (Drs)-Rp49 reporter gene after the injection of water (white bars), the synthetic muropeptide dimmer (stripes) or SLPG (black bars) into wild-type female adult flies and PGRP-SA$^{seml}$ mutant flies. Drs expression was measured in four flies collected 18 hrs after challenge and normalized to the value obtained after injection of water (set at 100%). Bars represent the mean±s.d. of four independent experiments.

FIG. 4 shows appearance of melanin pigment examined within 18 hrs after the injection of 100 ng of synthetic muropeptide dimmer (a) or SLPG (b) into *Tenebrio* larvae.

FIG. 9 (A) shows ability of *Drosophila* PGRP-SA to bind to the partially-digested is insoluble Lys-PG. Lyso (–) and Lyso (+) indicate intact and partially-digested insoluble Lys-PG, respectively. Lane 1 indicates *Drosophila* PGRP-SA only; Lanes 2 and 4 indicate the amounts of unbound ("U") *Drosophila* PGRP-SA when Lyso (–) or Lyso (+) PG was incubated with *Drosophila* PGRP-SA, respectively. Lanes 3 and 5 indicate the amounts of bound ("B") Dm-PGRP-SA on Lys (–) or Lys (+) PG, respectively. FIG. 9 (B) shows binding ability of *Tenebrio* PGRP-SA to the partially-digested insoluble Lys-PG. Each lane denotes the same meaning as in FIG. 9 (A).

FIG. 10 shows SDS/PAGE results analyzed after incubation with *Tenebrio* PGRP-SA-deficient hemolymph solution. Proteins were extracted from the intact insoluble PG (lane 1), *Tenebrio* PGRP-SA-bound PG (lane 2), or *Drosophila* PGRP-SA-bound PG (lane 3) after incubation with *Tenebrio* PGRP-SA-deficient hemolymph solution. *M. luteus* insoluble PG (lanes 4 and 5) and the synthetic muropeptide dimer-coupled resin (lanes 6 and 7) without and with *Tenebrio* PGRP-SA were treated. It is notable that the *Drosophila* PGRP-SA bound to the partially digested PG did not interact with the two *Tenebrio* proteins (lane 3).

FIG. 11 (A) shows comparison of the N-terminal sequences of band 1 (SEQ ID NO: 12) and *Tribolium casta*-

*neum* GNBP-like protein (Tc-GNBP, XP_969449) (SEQ ID NO: 13), *T. molitor* glucan recognition protein (Tm-GRP) (SEQ ID NO: 14), *Anopheles gambiae* GNBP1 (Ag-GNBP1, AAR13751) (SEQ ID NO: 15), and *Drosophila melanogaster* GNBP1 (Dm-GNBP1) (SEQ ID NO: 16). Boxes indicate residues identical to those in the sequence of band 1. FIG. 11 (B) shows N-terminal amino acid sequence comparison between band 2 (SEQ ID NO: 17) and *Tribolium castaneum* serine protease (Tc-SP, XP_967486) (SEQ ID NO: 18), *M. sexta* hemolymph protease 14 (Ms-HP14) (SEQ ID NO: 19), *A. gambiae* serine protease (Ag-SP, XP_321263) (SEQ ID NO: 20), and *D. melanogaster* modular serine protease (Dm-MSP, CG31217) (SEQ ID NO: 21). FIG. 11 (C) shows sequence identities between two internal sequences (Peak 1 (SEQ ID NO: 22) and Peak 2 (SEQ ID NO: 24)) of band 2 and low-density lipoprotein receptor A repeat domain sequence of Tc-SP (SEQ ID NO: 23 relative to Peak 1 and SEQ ID NO: 25 relative to Peak 2).

FIG. 13 shows the results obtained by injecting *Tenebrio* PGRP-SA only (A), a mixture of *Tenebrio* PGRP-SA and the linearized PG (B), a mixture of *Drosophila* PGRP-SA and the linearized PG (C), or *Tenebrio* PGRP-SA and linearized PG (D) onto the Toyopearl HW-55S size-exclusion column, respectively.

FIGS. 15 to 17 show the amino acid sequence (lower rows, SEQ ID NO: 2) and the nucleotide sequence (upper rows, SEQ ID NO: 3) of *Tenebrio* GNBP1.

FIGS. 18 to 21 show the amino acid sequence (lower rows, SEQ ID NO: 4) and the nucleotide sequence (upper rows, SEQ ID NO: 5) of *Tenebrio* MSP-1. Also indicated are those amino acids and nucleotides which differ in the variant MSP-2.

DETAILED DESCRIPTION OF THE INVENTION

Technical Problem

Figure 1:
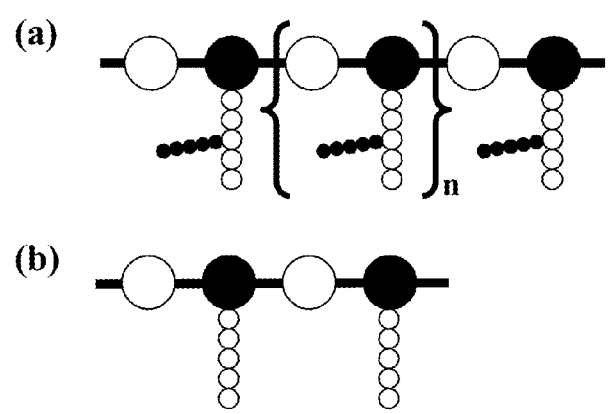
FIG. 1 is expected structures of linearized peptidoglycan (PG) (a) and synthetic muropeptide dimmer (b), in which white large circles, black large circles, black small circles and white small circles indicate N-acetyl-glucosamine, N-acetylmuramic acid, stem peptides, and Gly residues of *S. aureus* PG, respectively.

The present Inventors performed various studies on how a Lys-PG recognition signal is transferred downstream through a biochemical approach using in vivo *Drosophila* Toll pathway, in vitro pro-PO activation system and recombinant PGRP-SA proteins. As a result, we isolated proteins involved in a pro-PO system and also found that such proteins are useful for detecting bacterial infection in a sample, such as blood. Also, the present inventors developed a method of preparing a soluble linearized Lys-type peptidoglycan (SLPG), which is useful for a standard substance in detecting bacterial infection in a sample.

Therefore, the present invention provides proteins activating pro-phenoloxidase (pro-PO) system and genes encoding the same.

The present invention also provides a method of detecting bacterial infection in a sample using the proteins.

The present invention also provides a kit for detecting bacterial infection in a sample using the proteins.

The present invention also provides a method of preparing a soluble linearized Lys-type peptidoglycan (SLPG).

Advantageous Effects

Through the present invention, novel factors (i.e., proteins) activating a pro-PO system are identified. The proteins can be used to detect bacterial infection in a sample such as blood, or to manufacture a kit for the detection thereof. In addition, when a sample such as blood is pre-treated using blp and/or lysozyme according to the present invention, bacterial infection can be more effectively detected by the factors involved in a pro-PO system.

The present inventors revealed that a complex of a peptidoglycan recognition protein of *Tenebrio molitor* (*Tenebrio* PGRP-SA) and peptidoglycan (PG) activates a pro-PO system by recruiting proteins involved in signal transduction toward downstream. We also found that the proteins involved in signal transduction toward downstream are a Gram-negative bacteria binding protein 1 (GNBP1) homologue (i.e., *Tenebrio* GNBP1); and a *Tenebrio*-multi-domain containing modular serine protease (i.e., *Tenebrio* MSP) which has a low density lipoprotein-like domain and a complement control protein-like domain at its N-terminal. We also revealed that *Tenebrio* MSP exists in two forms, that is, *Tenebrio* MSP-1 and *Tenebrio* MSP-2. Furthermore, we revealed amino acid sequences of the *Tenebrio* GNBP1 and *Tenebrio* MSP and nucleotide sequences encoding the same. *Tenebrio* GNBP1 and *Tenebrio* MSP is seemed to form a complex together with the complex of *Tenebrio* PGRP-SA and PG.

Therefore, the present invention provides a *Tenebrio molitor*-derived Gram negative bacteria binding protein 1 (*Tenebrio* GNBP1), which has an amino acid sequence as set forth in SEQ ID NO: 2.

The present invention also provides a polynucleotide encoding the *Tenebrio* GNBP1 having an amino acid sequence as set forth in SEQ ID NO: 2, preferably a polynucleotide having a nucleotide sequence as set forth in SEQ ID NO: 3.

The present invention also provides a *Tenebrio molitor*-derived modular serine protease-1 (*Tenebrio* MSP-1), which has an amino acid sequence as set forth in SEQ ID NO: 4.

The present invention also provides a polynucleotide encoding the *Tenebrio* MSP-1 having an amino acid sequence as set forth in SEQ ID NO: 4, preferably a polynucleotide having a nucleotide sequence as set forth in SEQ ID NO: 5.

The present invention also provides a *Tenebrio molitor*-derived modular serine protease-2 (*Tenebrio* MSP-2), which has an amino acid sequence as set forth in SEQ ID NO: 6.

The present invention also provides a polynucleotide encoding the *Tenebrio* MSP-2 having an amino acid sequence as set forth in SEQ ID NO: 6, preferably a polynucleotide having a nucleotide sequence as set forth in SEQ ID NO: 7.

In accordance with an embodiment, there is provided a method of detecting bacterial infection in a sample, the method comprising: (a) loading a *Tenebrio molitor*-derived peptidoglycan recognition protein (*Tenebrio* PGRP-SA) having an amino acid sequence as set forth in SEQ ID NO: 1 to a sample and then performing an incubation thereof; (b) loading at least one protein selected from the group consisting of a *Tenebrio* GNBP1 having an amino acid sequence as set forth in SEQ ID NO: 2, a *Tenebrio* MSP-1 having an amino acid sequence as set forth in SEQ ID NO: 4, and *Tenebrio* MSP-2 having an amino acid sequence as set forth in SEQ ID NO: 6 to the incubation mixture of step (a) and then performing an incubation; and (c) detecting reactivity between the protein and the sample in the incubation mixture of step (b).

In the method of detecting bacterial infection in a sample, the sample may be a blood for transfusion; a mammalian blood, including human blood; food, such as vegetables, meats, fruits, or the like; cooked or non-cooked foods; water, such as tap water, underground water, rain water, or the like; sterile products; or the like. The sample may be any sample that is required for microorganism detection. Specifically, the method of detecting bacterial infection according to the present invention is suitable for detecting bacterial infection in a blood for transfusion or a mammalian blood including human blood.

In the method of detecting bacterial infection according to the present invention, the incubation(s) can be performed at about 30° C. for such a time that a sample can sufficiently react with the protein(s). If required, the incubation can be performed in various buffers containing EDTA as a calcium ion inhibitor.

Also, the detecting reactivity in step (c) can be performed in accordance with a conventional method using a size-exclusion column, such as a column filled with a size-exclusion Toyopearl HW55S resin.

If required, the method of detecting bacterial infection according to the present invention can further include pre-treating the sample with β-lytic protease (blp) and/or lysozyme. As described in Examples below, in most of intact peptidoglycan of Gram-positive bacterium, glycan chains are highly cross-linked, which may limit the access of a recognition protein (that is, a protein having an amino acid sequence as set forth in SEQ ID NO: 1, *Tenebrio* PGRP-SA) to the peptidoglycan. However, the treating a sample with β-lytic protease (blp) and/or lysozyme facilitates forming a complex with *Tenebrio* PGRP-SA.

The blp may be derived from various microorganisms, such as a soil microorganism. For example, the blp can be derived from a microorganism belonging to genus *Achromobacter*, preferably *Achromobacter lyticus*, and more preferably *Achromobacter lyticus* ATCC 21456 or *Achromobacter lyticus* ATCC 21457. Alternatively, the blp can be prepared by purifying a commercially available crude Achromopeptidase preparation (Wako Pure Chemical Institute, 014-09661) using a known method (Li, S., Norioka, S. & Sakiyama, F. (1998) *J Biochem* (Tokyo) 124, 332-339).

The pre-treatment with blp can be performed by treating the sample with blp in a concentration of about 1 μg/ml and then incubating at about 37° C. for about 14 hours.

The lysozyme used in the method of detecting bacterial infection of the present invention can be a commercially available lysozyme (for example, hen egg white to lysozyme). The pre-treatment with lysozyme may be performed by treating the sample with lysozyme in a concentration of about 1 mg/ml and then incubating at about 37° C. for a varying reaction time.

In accordance with another embodiment, there is provided a kit for detecting bacterial infection in a sample comprising: a *Tenebrio* PGRP-SA having an amino acid sequence as set forth in SEQ ID NO: 1, and at least one protein selected from the group consisting of a *Tenebrio* GNBP1 having an amino acid sequence as set forth in SEQ ID NO: 2, a *Tenebrio* MSP-1 having an amino acid sequence as set forth in SEQ ID NO: 4, and *Tenebrio* MSP-2 having an amino acid sequence as set forth in SEQ ID NO: 6.

In the detection kit of the present invention, the sample may be a blood for transfusion; a mammalian blood, including human blood; food, such as vegetables, meats, fruits, or the like; cooked or non-cooked foods; water, such as tap water, underground water, rain water, or the like; sterile products; or the like. The sample may be any sample that is required for microorganism detection. Specifically, the detection kit according to the present invention is suitable for detecting bacterial infection in a blood for transfusion or a mammalian blood including human blood.

The detection kit of the present invention may include a reagent for detecting reactivity, for example, an amino acid or peptide bound to p-nitroaniline, proteins activating a pro-PO system, and a chromogenic substrate of a pro-PO enzyme. The detection kit may be in a form of solution, freeze-dried powder, frozen solution, or a strip. Each of these forms can be formulated using any conventional method known in the art. For example, the detection kit in a form of a solution can be formulated by mixing the protein(s) with a buffer, such as a sodium-phosphoric acid buffer, a potassium-phosphoric acid buffer, a Tris-hydrochloric acid buffer, or the like, in a mixed form or in separate forms. If required, the solution can be frozen or freeze-dried.

The detection kit of the present invention may further include β-lytic protease (blp) and/or lysozyme. The blp may be derived from various microorganisms, such as a soil microorganism. For example, the blp can be derived from a microorganism belonging to genus *Achromobacter*, preferably *Achromobacter lyticus*, and more preferably *Achromobacter lyticus* ATCC 21456 or *Achromobacter lyticus* ATCC 21457. Alternatively, the blp can be prepared by purifying a commercially available crude Achromopeptidase preparation (Wako Pure Chemical Institute, 014-09661) using a known method (Li, S., Norioka, S. & Sakiyama, F. (1998) *J Biochem* (Tokyo) 124, 332-339). And also, the lysozyme can be a commercially available lysozyme.

The present invention also provides a method of preparing a soluble linearized Lys-type peptidoglycan (SLPG) that can be used as a standard substance of Lys-PG in is detecting bacterial infection in a sample. That is, the present invention provides a method of preparing a soluble linearized Lys-type peptidoglycan (SLPG), the method comprising: (a') suspending an insoluble peptidoglycan isolated from a bacteria in a buffer solution of about pH 8; (b') treating the suspension obtained from step (a') with β-lytic protease (blp); (c') heating the reaction mixture obtained from step (b') at about 95° C. for about 10 minutes, centrifuging the reaction mixture, and then collecting a supernatant; and (d') fractionizing the supernatant obtained from step (c') using a size-exclusion column to collect a fraction showing phenoloxidase (PO) activity.

In the method of preparing SLPG, the insoluble peptidoglycan isolated from bacteria can be prepared using any method known in the art (e.g., BL de Jonge, Y S Chang, D Gage, and A Tomasz, Peptidoglycan composition of a highly methicillin-resistant *Staphylococcus aureus* strain. The role of penicillin binding protein 2A *J. Biol. Chem.*, June 1992; 267: 11248-11254).

The buffer solution in step (a') can be a Tris buffer of about pH 8.0. And also, the blp may be derived from various microorganisms, such as a soil microorganism. For example, the blp can be derived from a microorganism belonging to genus *Achromobacter*, preferably *Achromobacter lyticus*, and more preferably *Achromobacter lyticus* ATCC 21456 or *Achromobacter lyticus* ATCC 21457. Alternatively, the blp can be prepared by purifying a commercially available crude Achromopeptidase preparation (Wako Pure Chemical Institute, 014-09661) using a known method (Li, S., Norioka, S. & Sakiyama, F. (1998) *J Biochem* (Tokyo) 124, 332-339).

The treating with blp can be performed by treating the suspension containing the insoluble peptidoglycan with blp in a concentration of about 1 μg/ml and then incubating at about 37° C. for about 14 hours.

In step (c'), the centrifuging can be performed at about 18,000×g, at a temperature of about 4° C., for about 10 minutes. If required, the supernatant obtained from the centrifugation may be freeze-dried and then stored at a temperature of about 4° C.

In step (d'), the size-exclusion column is a column filled with a Toyopearl HW55S resin. Typically, the column is used after being equilibrated with sterile distilled water. The fractionizing can be performed by eluting the solution obtained from step (c') (i.e., soluble PG solution) through the column. Among the fractions, the fraction showing phenoloxidase (PO) activity can be collected as follows: each fraction is diluted and then the hemolymph of *T. molitor* larvae is added thereto. After incubating the obtained mixture at 30° C. for 5 minutes, 20 mM Tris buffer (pH8.0) is added thereto. $CaCl_2$ solution, 4-methylcatechol (4-MC) solution, and 4-hydroxy proline ester (4-HP) solution are added thereto and mixed together. The mixture is left to sit in a constant temperature bath of 30° C. Absorbance is measured at a wavelength of 520 nm using a spectrophotometer at the time showing the largest color variance, compared to color variance of the hemolymph having $Ca^{2+}$ alone.

If required, the obtained fraction showing phenoloxidase (PO) activity may be further purified by concentrating the fraction, fractionizing through a column filled with a Toyopearl HW55S resin, and then isolating a SLPG-containing fraction.

And also, if required, the method of preparing SLPG may further comprise freeze-drying the fraction obtained from step (d').

Hereinafter, the present invention will be described more specifically with reference to the following examples. The following examples are for illustrative purposes only and are not intended to limit the scope of the invention.

EXAMPLES

1. Methods (1) Purification and Characterization of *Achromobacter* β-Lytic Protease (blp)

*Achromobacter* β-lytic protease (blp) was purified to homogeneity from a commercially available crude Achromopeptidase preparation (Wako Pure Chemical Institute) according to the method reported previously (Li, S., Norioka, S. & Sakiyama, F. (1998) *J Biochem* (Tokyo) 124, 332-339). To confirm the identity of the blp, the N-terminal sequence of the purified blp was determined on an Applied Biosystem Procise automated gas-phase amino acid sequencer. The bacteriolytic activity of blp against *Micrococcus luteus* was assayed by the method of Sakiyama (Li, S., Norioka, S. & Sakiyama, F. (1997) *J Biochem* (Tokyo) 122, 772-778).

(2) Purification of Soluble Linearized Lys-Type Peptidoglycan (SLPG)

(2-1) Incubation of Microorganism

*Staphylococcus aureus* ATCC 12598 (Cowan serotype) strain was inoculated in a liquid medium (TSB (tryptic soy broth) medium, 100 ml) and then incubated at 37° C. for 12 hours. 20 ml of the medium was inoculated to each of TSB medium 2 L (400 ml×5 bottles) and then incubated for 12 hours. The resultant medium was centrifuged at a rotation speed of 6000 rpm at a temperature of 4° C. for 30 minutes. Then, the cells were collected and the collected cells were suspended in 200 ml of sterile distilled water, and the resultant cells were collected again. Such processes (i.e., collecting and suspending) were performed 6 times. The obtained cells were suspended in 76.8 ml of 50 mM Tris buffer (pH 7.0) and the obtained suspension was loaded in the same amount to 50 ml of two test tubes.

(2-2) Isolation and Purification of Insoluble Peptidoglycan

The isolation and purification of insoluble peptidoglycan were performed according to a known method (BL de Jonge, Y S Chang, D Gage, and A Tomasz Peptidoglycan composition of a highly methicillin-resistant *Staphylococcus aureus* strain. The role of penicillin binding protein 2A *J. Biol. Chem.*, June 1992; 267: 11248-11254), which will be described in detail.

1.6 ml of 20% sodium dodecyl sulfate (SDS) solution which had been heated at 95° C. was added to the cell suspension obtained in the above to obtain a 4% bacterial solution, which was heated at 95° C. for 45 minutes and then sufficiently cooled in ice bath. The obtained bacterial solution was centrifuged (18,000×g, 4° C., 10 minutes). The supernatant was discarded and the resultant bacterial cells were collected. 40 ml of sterile distilled water was added to the collected bacterial cells. Centrifugation was performed in the same conditions as described above and the bacterial cells were collected. Such processes were performed 6 times. The collected bacterial cells were suspended in 40 ml of 1×PBS buffer and then reacted with DNase and RNase in a concentration of 100 μg/ml at 37° C. for 18 hours. The reaction mixture was reacted with 200 μg/ml of trypsin at 37° C. for 18 hours. 20% SDS solution which had been heated at 95° C. was added to the reaction mixture to obtain a 1% bacterial solution, and the solution was heated at 95° C. for 10 minutes to stop the enzymatic reaction. The obtained reaction mixture was centrifuged (18,000×g, 4° C., 10 minutes) and the resulting precipitate was collected. 40 ml of sterile distilled water was added to the precipitate, and the resultant solution was centrifuged (18,000×g, 4° C., 10 minutes) and the precipitates was collected. Such processes were performed three times. The obtained precipitate was suspended in 40 ml of 8M LiCl solution and then 40 ml of sterile distilled water was added thereto. The obtained suspension was centrifuged (18,000×g, 4° C., 10 minutes), and the resulting precipitate was collected. The collected precipitate was suspended in 40 ml of 100 mM EDTA (pH8.0) solution and then 40 ml of sterile distilled water was added thereto. The obtained suspension was centrifuged (18,000×g, 4° C., 10 minutes) and the resulting precipitate was collected. The collected precipitate was suspended in 40 ml of sterile distilled water. The obtained suspension was centrifuged (18,000×g, 4° C., 10 minutes), and the resulting precipitate was collected. The collected precipitate was suspended in 40 ml of acetone. The obtained suspension was centrifuged (18,000×g, 4° C., 10 minutes), and the resulting precipitate was collected. The collected precipitate was freeze-dried to obtain about 380-400 mg of insoluble peptidoglycan.

(2-3) Purification of SLPG

The obtained insoluble peptidoglycan was treated with β-lytic protease (blp). That is, 2 μg/ml of blp was added to a suspension of the obtained insoluble peptidoglycan (20 mg) in 20 mM Tris buffer (pH8.0), which was then incubated at a temperature of 37° C. for 14 hours. The reaction mixture was boiled at 95° C. for 10 minutes and then centrifuged (18,000× g, 4° C., 10 minutes). The supernatant was collected and then freeze-dried. The freeze-dried product was left to sit at 4° C.

A column (2.6×15.5 cm) was filled with 60 ml of Toyopearl HW55S resin and equilibrated using sterile distilled water at a flow speed of 0.5 ml/min, and then 1 mg of the soluble PG solution prepared as described above was loaded to the column and was fractionized in a predetermined volume. Each of fractions was diluted using sterile distilled water to obtain a 100× solution. 10 μl of each diluted solution was used to identify PO activity.

The PO activity was identified as follows: 30 μl of the hemolymph of *T. molitor* larvae (about 280 μg of hemolymph protein) was added to 10 μl of each of the diluted solutions, and then incubated at 30° C. for 5 minutes. 435 μl of 20 mM Tris buffer (pH8.0) was added thereto and immediately 5 μl of 1M $CaCl_2$ solution (10 mM of a final concentration) was added thereto. 4 of 250 mM 4-methylcatechol (4-MC) solution and 16 μl of 62.5 mM 4-hydroxy proline ester (4-HP) solution were added thereto, and mixed together. The mixture was left to sit in a constant temperature bath of 30° C. Absorbance was measured at a wavelength of 520 nm using a spectrophotometer at the time showing the largest color variance, compared to color variance of the hemolymph having $Ca^{2+}$ alone.

The fractions showing phenoloxidase (PO) activity were collected and concentrated using a rotary evaporator at 4° C. The concentrated solution was again loaded onto the same column equilibrated with distilled water at a flow rate of 0.2 ml/min. The SLPG-containing fractions were pooled and stored at 4° C. until use. To ascertain that the purified SLPG originated from *S. aureus* Lys-PG, we analyzed the amino acid composition of SLPG, which was the same amino acid composition (D-Glu:L-Gly:D-Ala:L-Lys=1:5:1:1) as reported for *S. aureus* Lys-PG (Schleifer, K. H. & Kandler, O. (1972) *Bacteriol Rev* 36, 407-477).

(3) Collection of Hemolymph, PO Activity Assay and Melanin Synthesis

*T. molitor* larvae (mealworm) were maintained on a laboratory bench in terraria containing wheat bran. Hemolymph was collected as previously described (Zhang, R., Cho, H. Y., Kim, H. S., Ma, Y. G., Osaki, T., Kawabata, S., Soderhall, K. & Lee, B. L. (2003) *J Biol Chem* 278, 42072-42079). An assay of PO was carried out according to our previously published method (Park, J. W., Je, B. R., Piao, S., Inamura, S., Fujimoto, Y., Fukase, K., Kusumoto, S., Soderhall, K., Ha, N. C. & Lee, B. L. (2006) *J Biol Chem* 281, 7747-7755). To test melanin synthesis, 2 μl of SLPG (50 μg/ml), 10 μl of insoluble Lys-PG (5 mg/ml), partially-digested insoluble Lys-PG (5 mg/ml) or 5 μl of the compound of Formula (I) (synthetic muropeptide dimmer) (20 μg/ml) was injected into live larvae. Six μl of N,N',N"-triacetyl chitotriose was injected at a 6 mM final concentration. After 24 hours, the appearance of melanin pigment was estimated.

(4) Injection of SLPG and the Compound of Formula (I)

Oregon$^R$ flies were used as the wild-type strain. PGRP-SA$^{smel}$ is a line carrying the semmelweis mutation (C54Y) in *Drosophila* PGRP-SA (Michel, T., Reichhart, J. M., Hoffmann, J. A. & Royet, J. (2001) *Nature* 414, 756-759). Ten nl of water, SLPG (10 mg ml-1) or the compound of Formula (I) (10 mg ml-1) was injected into the thorax of the wild-type or PGRP-SA$^{smel}$ female adults (2-4 days old) using a Nanoject apparatus (Drummond). After injection, the flies were then incubated for 18 h at 25° C. Drosomycin expression level was measured as previously described (Leulier, F., Parquet, C., Pili-Floury, S., Ryu, J. H., Caroff, M., Lee, W. J., Mengin-Lecreulx, D. & Lemaitre, B. (2003) *Nat Immunol* 4, 478-484).

(5) Formation of PGRP/SLPG Complexes

After incubation of 40 μg of *Drosophila* PGRP-SA or *Tenebrio* PGRP-SA with 400 μg of SLPG for 30 min at 30° C., the mixture was injected onto a Superdex S-200 HR 10/30 column that was equilibrated with 20 mM Tris buffer (pH 8.0) containing 150 mM NaCl. The fractions containing the PGRP-SA/SLPG complex were pooled. The presence of PGRP-SA was monitored by SDS-PAGE.

(6) Partial Digestion of SLPG and Insoluble Lys-PG by Lysozyme

To obtain soluble oligomeric Lys-PG fragments showing PO activity, 10 μl of hen egg white lysozyme (1 mg ml$^{-1}$, Wako) was added to 100 μl of purified SLPG (800 μg ml$^{-1}$) and then incubated for 5 min at 37° C. The partially-digested SLPG was boiled for 10 min and then loaded on a Toyopearl HW-55S column equilibrated with 20 mM Tris buffer (pH 8.0) at a flow rate of 0.5 ml/min. The fractions showing PO activity were pooled. To obtain partially-digested insoluble polymeric Lys-PG, *S. aureus* insoluble PG (40 mg), suspended in PBS buffer (pH 7.2), was incubated with 10 μg of lysozyme for 3 hours at 37° C. After boiling for 10 min and then centrifuging at 20,000×g for 10 min at 4° C., the residue in the pellet fraction was washed 3 times with 8 M urea and 3 times with distilled water.

(7) Binding Assay of PGRPs to Partially Digested Insoluble Lys-PG

The binding assay was performed according to the previously reported method (Park, J. W., Je, B. R., Piao, S., Inamura, S., Fujimoto, Y., Fukase, K., Kusumoto, S., Soderhall, K., Ha, N. C. & Lee, B. L. (2006) *J Biol Chem* 281, 7747-7755). Briefly, 10 μg of the purified *Tenebrio* PGRP-SA or *Drosophila* PGRP-SA was mixed with 40 μl of a 50% (v/v) suspension of the partially-digested *S. aureus* or *M. luteus* PG (500 μg) in 50 mM Tris-HCl buffer (pH 7.0) for 12 h at 4° C. in a shaker. Unbound PGRP in the supernatant and bound PGRP in the pellet fraction were analyzed by SDS-PAGE.

(8) Identification of *Tenebrio* GNBP1 and Associated Modular Serine Protease

A *Tenebrio* PGRP-SA (−) solution was prepared from the hemolymph of *T. molitor* according to the previously reported method by using a compound of Formula (I)-coupled affinity column (Park, J. W., Je, B. R., Piao, S., Inamura, S., Fujimoto, Y., Fukase, K., Kusumoto, S., Soderhall, K., Ha, N. C. & Lee, Chemical Formula 1

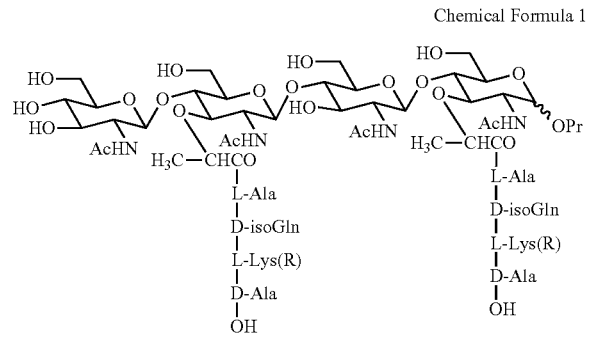

B. L. (2006) *J Biol Chem* 281, 7747-7755). This solution contains all of the essential components, except for *Tenebrio* PGRP-SA, necessary for the activation of the pro-PO system by Lys-PG. *Tenebrio* PGRP-SA (40 μg) was incubated with partially-digested insoluble Lys-PG (8 mg) in 200 μl of PBS buffer for 12 h at 4° C. After incubation, *Tenebrio* PGRP-SA-bound insoluble Lys-PG was recovered by centrifugation at 20,000×g for 10 min at 4° C., washed 3 times first with 20 mM Tris (pH 8.0) and next with 50 mM Tris-HCl buffer (pH 6.0). The recovered *Tenebrio* PGRP-SA-bound Lys-PG was incubated with 2.5 ml of the *Tenebrio* PGRP-SA (−) solution (20 mg of total protein) for 3 h at 4° C. After removing the insoluble residue by centrifugation, the mixture was washed twice with 50 mM Tris-HCl buffer (pH 6.0). The bound proteins on the insoluble Lys-PG were extracted with 100 μl of 2×SDS-PAGE loading buffer and then separated by SDS-PAGE. The protein bands on the polyacrylamide gel were transferred onto a polyvinylidene difluoride membrane and then the N-terminal sequences of the 50 kDa (*Tenebrio* GNBP1) and 35 kDa proteins (Tenebrio modular serine protease, *Tenebrio* MSP) were determined on an automatic gas-phase amino acid sequencer (Applied Biosystem).

(9) cDNA Cloning and Nucleotide Sequencing of *Tenebrio* GNBP1 and *Tenebrio* MSP For cDNA cloning of *Tenebrio* GNBP1, PCR was carried out using the degenerate sense primer 5'-GARGCNTAYGA-RCCNAARGG-3' (SEQ ID NO: 8) and the degenerate antisense primer 5'-ATRTCYTCYTGRTTRTTNGC-3' (SEQ ID NO: 9) (R=NG; Y=C/T; N=A/T/G/C) in a known method (Buck and Axel, *Cell* 65: 175-187, 1991; Riddle et al., *Cell* 75: 1401-1416, 1993; Krauss et al., *Cell* 75:1431-1444, 1993). For 5'- and 3'-RACE we used the SMART RACE cDNA amplification method (CLONTECH). All PCR products were cloned into pCR2.1-TOPO (Invitrogen), using the TOPO TA Cloning method (Invitrogen). Sequencing was carried out using the 3130xl Genetic Analyzer Sequencing method (Applied Biosystems).

cDNA cloning of *Tenebrio* MSP was also performed in the same manner, using 5'-AARGAYAAYTGYGAYGARAT-3' (SEQ ID NO: 10) and 5'-GCYTGYTGCCANGGRTARTC-3' (SEQ ID NO: 11) as degenerate sense and antisense primers, respectively.

2. Results and Discussion (1) SLPG Activates the Toll Pathway and the Pro-PO System

*Achromobacter* blp is a lysostaphin-like enzyme that hydrolyzes the peptide bonds in the penta-Gly bridge present in *S. aureus* PG (Li, S., Norioka, S. & Sakiyama, F. (1998) *J Biochem* (Tokyo) 124, 332-339). Therefore, the blp was expected to generate soluble polymeric PG fragments from insoluble PG with Gly residue(s) attached to the stem peptides (FIG. 1). Solubilized polymeric Lys-PG fragments (SLPG) were obtained by using blp from *S. aureus* PG. SLPG is anticipated to be a polymerized muropeptide linked by β-1,4 glycosidic bonds between the sugars, not by penta-Gly bridges between the stem peptides. Therefore, SLPG should have multiple binding sites for PGRP-SA because it contains several muropeptide motifs. Using further purified SLPG, we confirmed that the recombinant *Drosophila* PGRP-SA and *Tenebrio* PGRP-SA proteins, which were expressed and purified in a baculovirus insect cell culture system, both bind to SLPG which was demonstrated using a size-exclusion column (FIGS. 13 (B) and (C)). However, a mixture of *Tenebrio* PGRP-SA and the compound of Formula (I) showed the same elution profile as *Tenebrio* PGRP-SA alone, suggesting that the compound of Formula (I) can bind to only one molecule of *Tenebrio* PGRP-SA.

Figure 2:
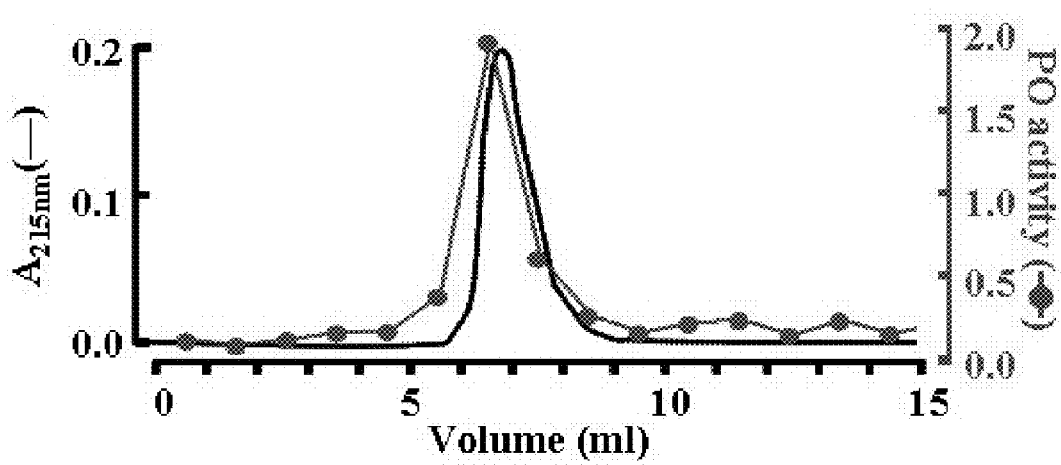
FIG. 2 is the UV absorbance profile of fractionized SLPG on a Toyopearl HW-55S size-exclusion column and the PO activity of each SLPG fraction.

We found that SLPG consistently induced a robust PO activity when added to *Tenebrio* hemolymph (FIG. 2). Subsequently, we injected SLPG into wild-type and is PGRP-SA$^{seml}$ mutant flies and then monitored expression of the drosomycin-encoding gene in order to test whether SLPG can activate the *Drosophila* Toll pathway in vivo (FIG. 3). The SLPG-injected wild-type flies induced drosomycin expression normally, but PGRP-SA$^{seml}$ mutant flies were defective in the induction of the antimicrobial peptide, demonstrating that SLPG activates the Toll pathway in a *Drosophila* PGRP-SA-dependent manner. In sharp contrast, the compound of Formula (I) failed to induce drosomycin expression in both the wild-type and the PGRP-SA$^{seml}$ mutant flies (FIG. 3). Likewise, SLPG strongly induced melanin synthesis when injected into the larvae of *Tenebrio*, most likely by activation of the pro-PO system (FIG. 4). These results suggest that the PG fragment containing multiple binding sites for PGRP-SA and that it can induce the Toll and pro-PO pathways. Recently, Ligoxygakis and his colleagues suggested that PG should be processed to increase the number of reducing ends to activate the Toll signaling pathway (Filipe, S. R., Tomasz, A. & Ligoxygakis, P. (2005) *EMBO Rep* 6, 327-333). Since both SLPG and the compound of Formula (I) contain one reducing end each but only SLPG is able to induce activation of both Toll and pro-PO cascade, this may suggest that the reducing ends may not be important.

Figure 5:
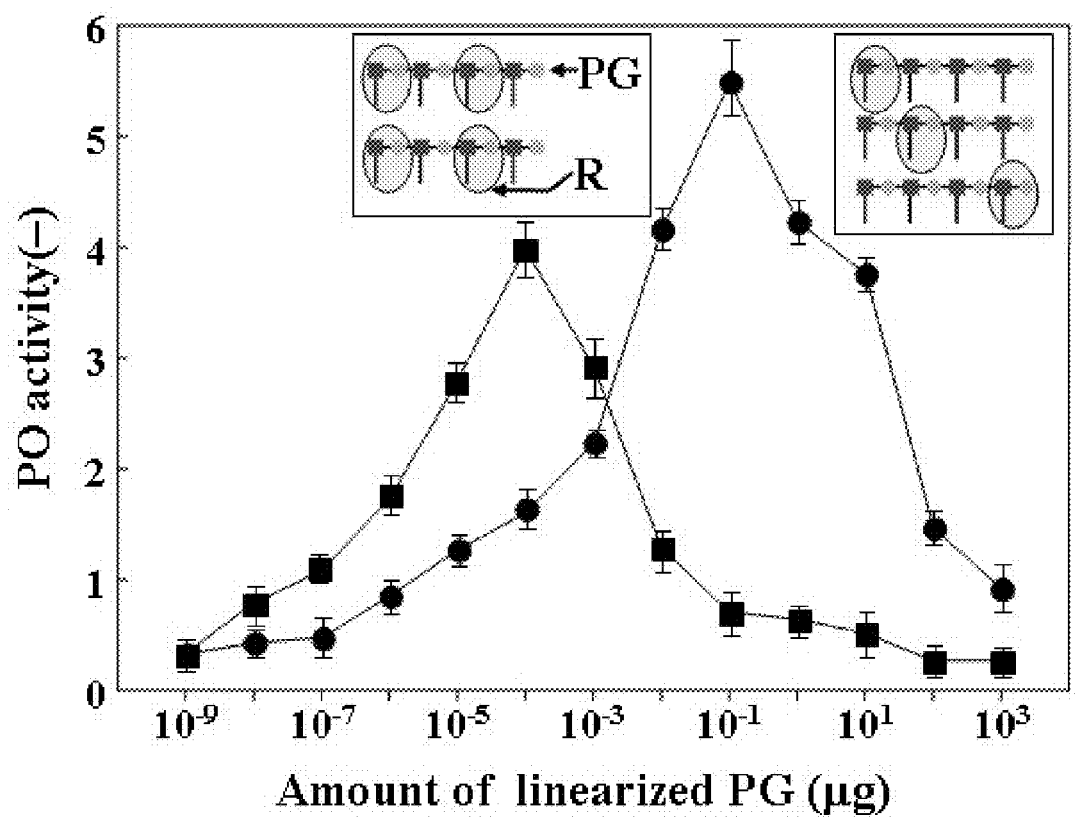
FIG. 5 shows Lys-PG-dependent PO activity measured with 10 nM of *Tenebrio* PGRP-SA (0.2 μg ml$^{-1}$) and different amounts of SLPG (squares). A bell-shaped dose-response curve was shifted to the right by the addition of *Tenebrio* PGRP-SA. By increasing the *Tenebrio* PGRP-SA concentration to 120 nM (2.5 μg ml$^{-1}$), a maximal point was observed at 100 ng of SLPG (circles). Insets indicate the putative complexed structures of *Tenebrio* PGRP-SA and SLPG.

(2) Proximal Binding of *Tenebrio* PGRP-SA is Needed for the Activation of the pro-PO Cascade We determined the minimal concentration of SLPG for activation of the PG-dependent pro-PO cascade. PO activity was measured by incubation of *Tenebrio* PGRP-SA protein in the *Tenebrio* PGRP-SA (−) solution with different amounts of SLPG. Surprisingly, the PO activity was severely inhibited to the baseline level at high concentrations of SLPG, showing a classic bell-shaped dose-response curve (FIG. 5). Moreover, the concentration of SLPG where the maximum PO activity was produced could be significantly elevated with a stronger PO activity if exogenous *Tenebrio* PGRP-SA protein was added to the reaction mixture (FIG. 5). These observations imply that too much SLPG acts as a competitive inhibitor sequestering PGRP-SA molecules, impairing the initial activating complex composed of *Tenebrio* PGRP-SA and Lys-PG. It also indicates that the amount of *Tenebrio* PGRP-SA per a binding unit of Lys-PG is important in forming the initial activation complex for the pro-PO cascade (the insets of FIG. 5). Similar observations were reported in β-1,3-glucan recognition by the horseshoe crab Factor G and crayfish pro-PO system (Muta, T., Seki, N., Takaki, Y., Hashimoto, R., Oda, T., Iwanaga, A., Tokunaga, F. & Iwanaga, S. (1995) *J Biol Chem* 270, 892-897; and Soderhall, K. & Unestam, T. (1979) *Can J. Microbiol.* 25, 406-414).

Figure 6:
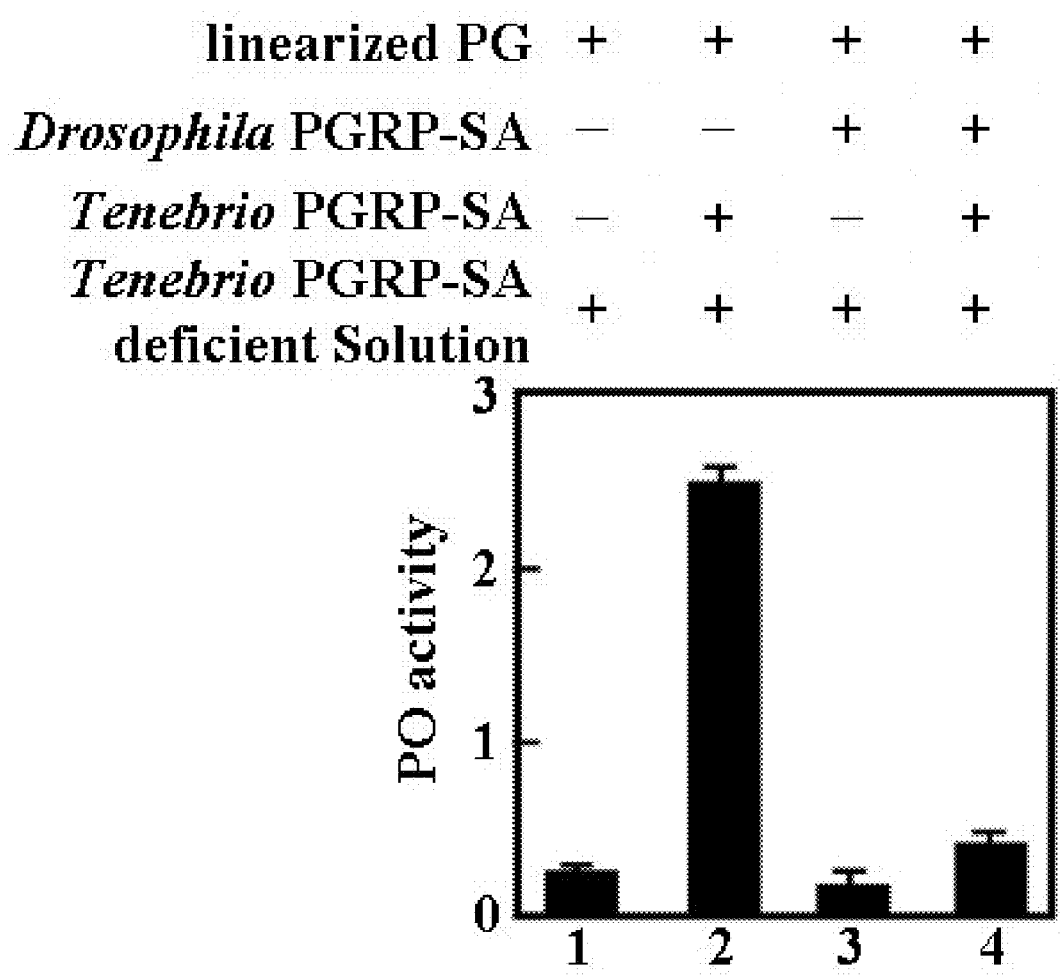
FIG. 6 shows In vitro reconstitution experiments performed by using *Tenebrio* PGRP-SA, *Drosophila* PGRP-SA and the *Tenebrio* PGRP-SA (–) solution in the presence of SLPG (columns 2 and 3, respectively). *Tenebrio* PGRP-SA and *Drosophila* PGRP-SA were co-incubated in the presence of SLPG (column 4).

We further investigated the initial activation step for Lys-PG recognition using recombinant *Drosophila* PGRP-SA that is able to bind SLPG with a similar affinity as *Tenebrio* PGRP-SA (FIG. 4), but the *Drosophila* PGRP-SA can not induce activation of the *Tenebrio* pro-PO cascade (3rd column of FIG. 6). The PO activity induced by SLPG was severely inhibited by the addition of *Drosophila* PGRP-SA to the *Tenebrio* PGRP-SA (−) solution even in the presence of exogenous *Tenebrio* PGRP-SA. This implies that the initial activating complex of the pro-PO cascade is abolished by replacement of the site for *Tenebrio* PGRP-SA by *Drosophila* PGRP-SA despite the presence of bound *Tenebrio* PGRP-SA to SLPG. These results strongly suggest again that clustering of PGRP-SA on Lys-PG or proximal binding of PGRP-SA to Lys-PG is required for the initial activating complex.

Figure 7:
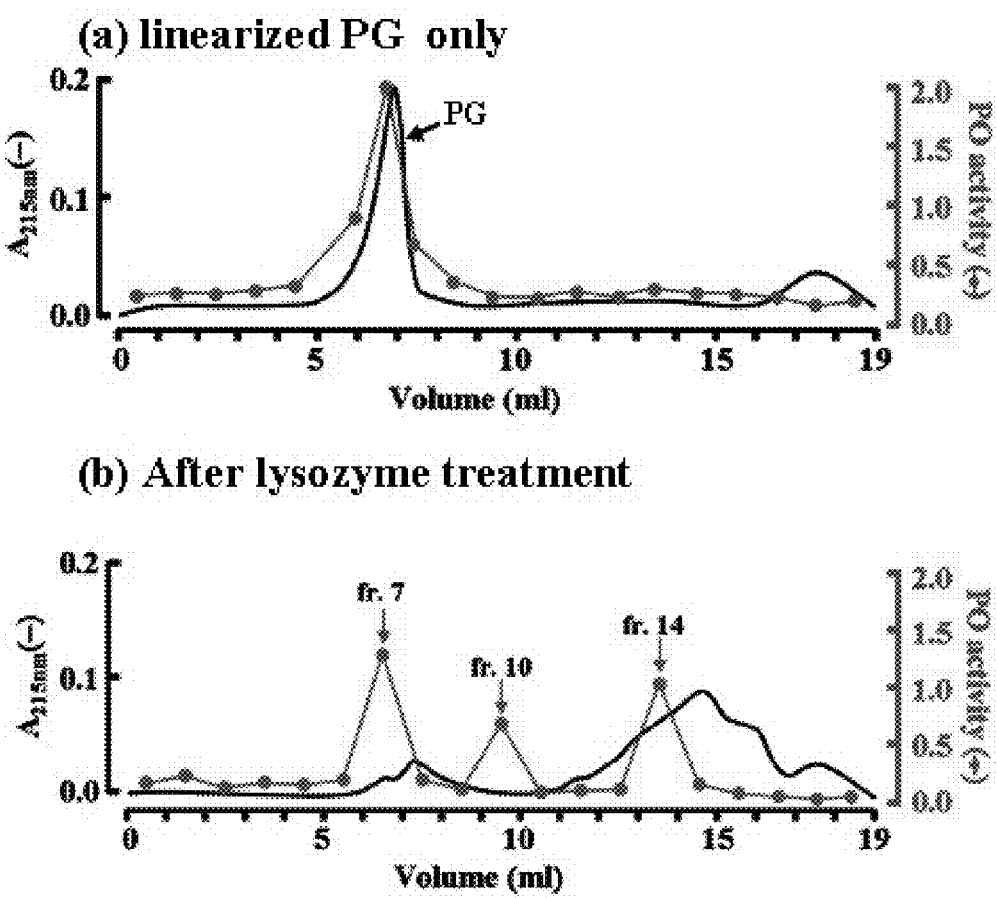
FIG. 7 shows linearized PG only (a) and partially-digested linearized PG by lysozyme (b), each fractionized by a Toyopearl HW-55S column equilibrated with 20 mM Tris buffer (pH 8.0) containing 150 mM NaCl.
Figure 8:
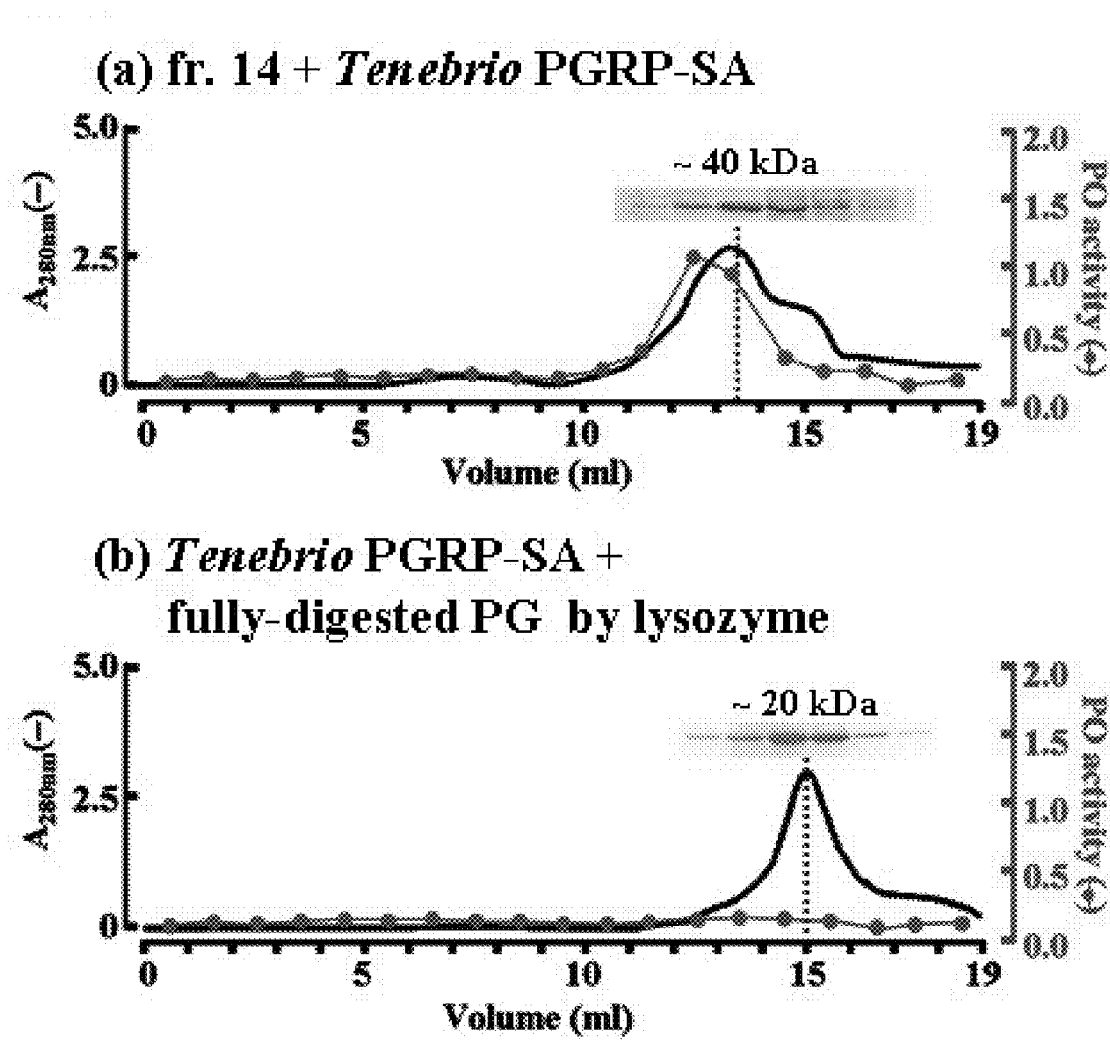
FIG. 8 (*a*) shows the results when a mixture of *Tenebrio* PGRP-SA and Fr. 14 was injected onto the same column and FIG. 8 (*b*) shows the results when a mixture of *Tenebrio* PGRP-SA and the fully-digested SLPG with lysozyme by incubation for 16 h at 37° C. was injected onto the same column.

(3) Lys-PG Fragments that Accommodate at Least Two *Tenebrio* PGRP-SA Molecules Activates the Pro-PO System To determine how many molecules of *Tenebrio* PGRP-SA constitute the initial activating complex for the pro-PO system, the various lengths of sugar chains of PG were generated by partial-digestion of SLPG with lysozyme and were then fractionized according to their length on a size exclusion column (FIGS. 7 (a) and (b)). Three fractions (7, 10 and 14th fractions) showed PO activity when each fraction was incubated with the *Tenebrio* PGRP-SA (−) solution in the presence of the *Tenebrio* PGRP-SA protein and $Ca^{2+}$. Of these, PG fragments in fraction 14 should be a to smallest unit that is able to induce activation of the pro-PO cascade. After adding an excess amount of *Tenebrio* PGRP-SA protein, we analyzed how many PGRP-SA molecules can bind to the PG fragments in fraction 14 by monitoring the apparent molecular weight on a size-exclusion column. The apparent molecular weight of the complex between the PG fragments in the fraction mixed with *Tenebrio* PGRP-SA was determined as about 40 kDa, which indicates that the PG fragment binds to two molecules of PGRP-SA. When the PG-fragment/*Tenebrio* PGRP-SA complex was incubated with the *Tenebrio* PGRP-SA (−) solution, it induced the PO activity even without adding *Tenebrio* PGRP-SA, clearly demonstrating that two molecular of *Tenebrio* PGRP-SA are sufficient to induce this activity (FIG. 9 (B)). However, the compound of Formula (I) and a muropeptide monomer that was generated by a prolonged incubation of SLPG with lysozyme did not change the molecular weight of *Tenebrio* PGRP-SA protein on the size-exclusion column (FIG. 9 (B)). This observation indicates that the compound of Formula (I) and the muropeptide monomer bind to only one PGRP-SA molecule. It is noteworthy that the compound of Formula (I) only bound to one PGRP-SA molecule although it contains two copies of muropeptide. We propose that this is a result of a steric hindrance by the first bound PGRP-SA molecule on the compound of Formula (I) because the two binding units on the compound of Formula (I) are located too closely. However, the muropeptide dimer that is cross-linked by a penta-Gly bridge is expected to accommodate two PGRP-SA molecules because the penta-Gly bridge provides sufficient space for binding of two PGRP-SA molecules. Consistently, the compound of Formula (I) was unable to activate the Toll and pro-PO pathways as shown above, whereas the muropeptide dimer was reported to induce activation of the Toll pathway (Filipe, S. R., Tomasz, A. & Ligoxygakis, P. (2005) *EMBO Rep* 6, 327-333). Thus, it can be concluded that the PG fragment that accommodates two PGRP-SA molecules is the minimum unit which could induce the downstream events and result in activation of the pro-PO system.

(4) Lysozyme Presents a Processed Form of PG for PG Recognition Signals

Figure 14:
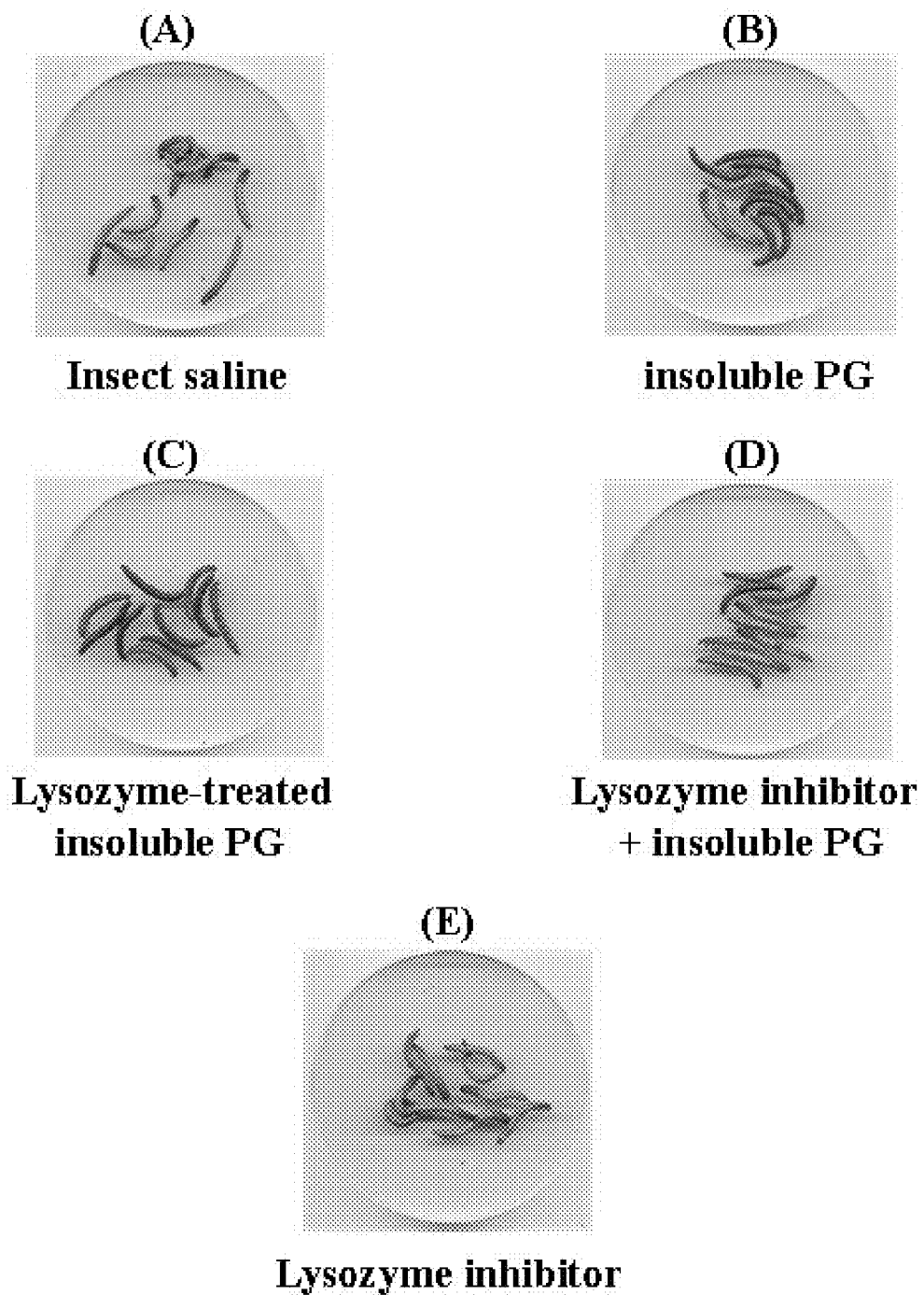
FIG. 14 shows the effects of lysozyme inhibitor on the Lys-type PG-dependent melanin synthesis. (A) Insect saline. (B) Insoluble Lys-PG. (C) Partially digested insoluble Lys-type PG. (D) Co-injection of lysozyme inhibitor and insoluble Lys-type PG. (E) Lysozyme inhibitor only.

Most natural Gram-positive bacterial PG is highly cross-linked between the glycan chains, which is different from that of SLPG. PGRP-SA might have limited access to natural Lys-PGs because of their highly cross-linked structure. Moreover, we previously observed that insoluble Lys-PGs, which had been disrupted by sonication induced a strong PO activity in vitro, while intact insoluble Lys-PG did not induce pro-PO activation at a given time (Park, J. W., Je, B. R., Piao, S., Inamura, S., Fujimoto, Y., Fukase, K., Kusumoto, S., Soderhall, K., Ha, N. C. & Lee, B. L. (2006) *J Biol Chem* 281, 7747-7755). In order to loosen the PG structure by an enzyme present in insect hemolymph, we chose lysozyme because it is able to hydrolyze almost all types of intact bacterial PG (Keep, N. H., Ward, J. M., Cohen-Gonsaud, M. & Henderson, B. (2006) *Trends Microbiol* 14, 271-276). We performed partial digestion of Lys-PG from both *S. aureus* and *M. luteus* with lysozyme in vitro. Indeed, the partially-digested Lys-PGs induced a rapid and strong PO activity in the *Tenebrio* hemolymph in vitro (data not shown). Moreover, when the partially-digested insoluble Lys-PGs were injected into *Tenebrio* larvae, stronger and faster melanin synthesis was observed in all of the injected larvae compared with intact insoluble Lys-PGs (FIGS. 14 (B) and (C)). However, when an inhibitor of lysozyme, N,N',N"-triacetylchitotriose, was co-injected with the intact Lys-PG, no melanin synthesis could be observed (FIG. 14 (D)), suggesting that intact Lys-PGs can not activate the pro-PO cascade without the enzymatic activity of lysozyme without prior partial degradation by lysozyme.

To ascertain the role of lysozyme in the recognition of Lys-PG by PGRP-SAs in vitro, we examined the binding of PGRP-SAs to the partially-digested Lys-PG using *Drosophila* PGRP-SA and *Tenebrio* PGRP-SA. To our surprise, the partial digestion of Lys-PG by lysozyme dramatically increased binding of both *Drosophila* PGRP-SA and *Tenebrio* PGRP-SA to PG (lanes 5 and 3 in FIGS. 9 (A) and (B), respectively). The enhanced interaction between PGRP-SAs and PG should result in proximal binding of PGRP-SAs in PG, leading to the activation of the Toll and pro-PO pathways. Our study presents the in vitro biochemical evidence that lysozyme plays a crucial role in enhancing the access of *Drosophila* PGRP-SA or *Tenebrio* PGRP-SA to insoluble Lys-PG in the Toll and pro-PO pathways, although it can not be excluded as a possibility that other proteins showing lysozyme-like activity process PGs for PGRP-SA binding.

Recently, a report appeared showing that *Drosophila* GNBP1 has an enzymatic activity that hydrolyzes loosely cross-linked *M. luteus* Lys-PG, but not highly cross-linked *S. aureus* Lys-PG (Wang, L., Weber, A. N., Atilano, M. L., Filipe, S. R., Gay, N. J. & Ligoxygakis, P. (2006) *EMBO J* 25, 5005-5014). Since they found that GNBP1 has lysozyme-like activity, they proposed that *Drosophila* GNBP1 presents a processed form of PG for sensing by *Drosophila* PGRP-SA. Considering the limited lysozyme-like activity of GNBP1 and also the fact that lysozyme in hemolymph is active on highly cross-linked PGs, GNBP1 may have less importance for processing PG than the hemolymph lysozyme. However the limited lysozyme-like activity of GNBP1 may play an important role in amplifying or scavenging the recognition signal.

(5) *Tenebrio* PGRP-SA/PG Complex Recruits *Tenebrio* GNBP1 and *Tenebrio* Multi Domain Modular Serine Protease (MSP)

In order to identify the immediate downstream effector(s) that recognizes the clustered *Tenebrio* PGRP-SA molecules on partially-digested Lys-PGs, recombinant *Tenebrio* PGRP-SA was incubated with the partially-digested *S. aureus* PG and *M. luteus* PG and then added to the *Tenebrio* PGRP-SA (−) solution and was then subjected to SDS-PAGE analysis.

As a result, a 50 kDa protein (band 1 in FIG. 10) and a 35 kDa protein (band 2 in FIG. 10) were specifically enriched if *Tenebrio* PGRP-SA was bound to a partially-digested Lys-PG (lanes 2 and 5 in FIG. 10). However, *Tenebrio* PGRP-SA bound to the compound of Formula (I)-coupled Sepharose resin failed to recruit the 50 kDa and 35 kDa proteins (lane 7 in FIG. 10) under the same conditions, demonstrating that the two proteins are recruited as a result of clustered PGRP-SA molecules on Lys-PG. Additionally, the *Drosophila* PGRP-SA bound to the partially-digested PG did not interact with the two *Tenebrio* proteins (lane 3 in FIG. 10).

We identified the two proteins enriched on the clustered *Tenebrio* PGRP-SA on Lys-PG. The 50 kDa protein (band 1) was a *Tenebrio* GNBP1 (*Tenebrio* GNBP1). The N-terminal 30 residues of the 50 kDa protein (band 1) exhibited 86.7% and 51.7% sequence identity with *Tribolium castaneum* GNBP and *Anopheles* GNBP1 proteins, respectively (FIG. 11 (A)). GNBP1 was reported to physically interact with PGRP-SA for the activation of the Toll pathway in *Drosophila* (Gobert, V., Gottar, M., Matskevich, A. A., Rutschmann, S., Royet, J., Belvin, M., Hoffmann, J. A. & Ferrandon, D. (2003) *Science* 302, 2126-2130), but any strong binding of GNBP1 to PGRP-SA has not previously been observed. Our observation supports that clustering of PGRP-SA molecules on PG enhances the interaction of PGRP-SA with GNBP1 and that the GNBP1 homologue may also be involved in the pro-PO pathway. And also, we revealed that the 35 kDa protein (band 2) is an active form of a multi-domain modular SP through N-terminal and internal amino acid sequencing. The N-terminal 20 residues of the 35 kDa protein (band 2) showed 70.6% sequence identity with the serine protease domain of *T. castaneum* serine protease (Tc-SP, accession number XP_967486; FIG. 11 (B)). Tc-SP contains low density lipoprotein receptor A repeat (LDLa) domains, one sushi domain, one complement control protein (CCP) domain and a SP domain, but it does not contain a clip domain that is commonly found in members of the Toll and pro-PO cascades. The identity of the 35 kDa protein was further confirmed through the presence of low-density lipoprotein receptor A repeat domain sequence in the protein band under non-reducing condition (FIG. 11 (C)). We designated the 35 kDa protein as *Tenebrio* modular serine protease. *Manduca sexta* hemolymph protease-14 (Ms-HP-14), showing a similar domain arrangement to that of *Tenebrio* modular serine protease, was recently reported as an initiation enzyme of the pro-PO activation system in *M. sexta* that binds curdlan, zymosan and yeast and interacts with peptidoglycan (Ji, C., Wang, Y., Guo, X., Hartson, S. & Jiang, H. (2004) *J Biol Chem* 279, 34101-34106; and Wang, Y. & Jiang, H. (2006) *J Biol Chem* 281, 9271-9278). In this study, we presented the first evidence that the Ms-HP-14-like serine protease is recruited to an initial activation complex consisting of the GNBP1 homologue, PGRP-SA and PG in the pro-PO pathway.

Figure 12:
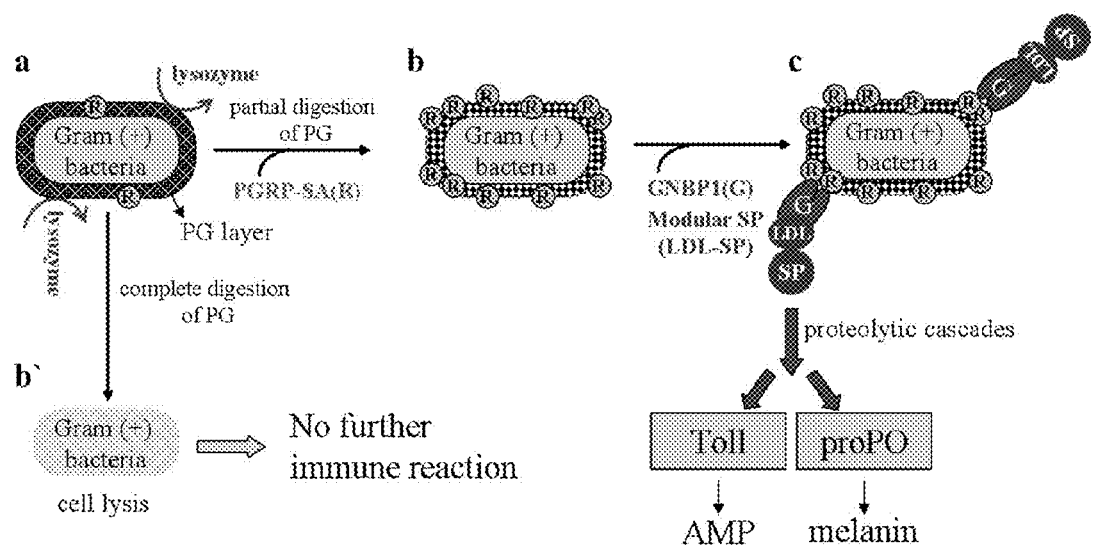
FIG. 12 shows a model summarizing the molecular events in the initiation of the Toll and pro-PO pathways.

The present inventors propose a model summarizing the molecular events in the initiation of the Toll and pro-PO pathways as follows (see FIG. 12). Although a few PGRP-SA (R) molecules bind to intact PG, it is not able to activate the immune responses (a). PG of Gram-positive bacteria is digested partially (b) or completely (b') by lysozyme. Whereas the partially digested PG recruits more PGRP-SA molecules binding to the bacterial surface (b), the fully digested PG cannot recruit PGRP-SA on the bacterial surface leading to lysis of the bacterial cell (b'). The clustered PGRP-SA molecules recruit GNBP1 and a modular serine protease (MSP) containing low-density lipoprotein receptor A repeat domains (LDL), resulting in the activation of the modular serine protease (c). Then the activated serine protease triggers the proteolytic cascade leading to activation of the Toll and prophenoloxidase (pro-PO) pathways that produce is antimicrobial peptide (AMP) and melanin around the invading bacteria.

(6) cDNA Cloning and Sequencing of *Tenebrio* GNBP1 and *Tenebrio* MSP

As a result of *Tenebrio* GNBP1 cDNA cloning, it was identified that the polynucleotide of *Tenebrio* GNBP1 consists of 1326 nucleic acids (SEQ ID NO: 3) encoding from Met to stop codon, and the polypeptide thereof consists of 442 amino acids (SEQ ID NO: 2).

As a result of *Tenebrio* MSP cDNA cloning, it was identified that there are two variants consisting of 1896 nucleic acids and 632 amino acids: a variant consisting of an amino acid sequence as set forth in SEQ ID NO: 4/a nucleotide sequence SEQ ID NO: 5 and the other variant consisting of an amino acid sequence SEQ ID NO: 6/a nucleotide sequence SEQ ID NO: 7. Such variants may be generated because the obtained genes are obtained from various kinds of insects and thus different combination of alleles by polymorphism between individuals occurs.

The invention claimed is:

1. An isolated *Tenebrio molitor*-derived Gram negative bacteria binding protein 1 (*Tenebrio* GNBP1), which has the amino acid sequence as set forth in SEQ ID NO: 2 in complex with *Tenebrio* PGRP-SA and peptidoglycan.

2. The isolated *Tenebrio* GNBP1 of claim 1, which is encoded by the nucleotide sequence as set forth in SEQ ID NO: 3.

* * * * *

SEQUENCE LISTING

```
<160> NUMBER OF SEQ ID NOS: 25

<210> SEQ ID NO 1
<211> LENGTH: 193
<212> TYPE: PRT
<213> ORGANISM: Tenebrio molitor

<400> SEQUENCE: 1

Met Leu Leu Ala Thr Ile Ala Arg Gly Val Tyr Gln Ile Ser Ala Leu
1               5                   10                  15

Ser Gly Ser Thr Ile Pro Arg Ile Cys Pro Glu Ile Ile Ser Arg Thr
            20                  25                  30

Arg Trp Gly Ala Arg Thr Pro Leu Glu Val Asp Tyr Ser Leu Ile Pro
        35                  40                  45

Ile Glu Asn Val Val Val His His Thr Val Thr His Thr Cys Asp Ser
    50                  55                  60
```

```
Glu Ser Glu Cys Ala Thr Leu Leu Arg Asn Val Gln Asn Phe His Met
 65                  70                  75                  80

Glu Asn Leu Glu Phe His Asp Ile Gly Tyr Asn Phe Leu Val Ala Gly
                 85                  90                  95

Asp Gly Gln Ile Tyr Glu Gly Ala Gly Trp His Lys Val Gly Ala His
            100                 105                 110

Thr Arg Gly Tyr Asn Thr Arg Ser Leu Gly Leu Ala Phe Ile Gly Asn
        115                 120                 125

Phe Thr Ser Gln Leu Pro Val Gln Lys Gln Leu Lys Val Ala Lys Asp
    130                 135                 140

Phe Leu Gln Cys Gly Val Glu Leu Gly Glu Leu Ser Lys Asn Tyr Lys
145                 150                 155                 160

Leu Phe Gly Ala Arg Gln Val Ser Ser Thr Ser Pro Gly Leu Lys
                165                 170                 175

Leu Tyr Arg Glu Leu Gln Asp Trp Pro His Phe Thr Arg Ser Pro Pro
                180                 185                 190

Lys

<210> SEQ ID NO 2
<211> LENGTH: 442
<212> TYPE: PRT
<213> ORGANISM: Tenebrio molitor

<400> SEQUENCE: 2

Met Phe Ala Lys Ala Ile Ile Leu Phe Leu Ile Leu Thr Thr Phe Gln
 1               5                  10                  15

Cys His Gly Glu Phe Val Ile Pro Glu Val Thr Leu Glu Ala Tyr Glu
                20                  25                  30

Pro Lys Gly Phe Arg Ala Ser Ile Pro Ala Leu Asn Gly Ile Gln Met
            35                  40                  45

Phe Ala Phe His Gly Asn Ile Asn Lys Pro Ile Ser Gln Val Asp Pro
        50                  55                  60

Gly Glu Tyr Ser Gln Asp Tyr Thr Ser Pro Thr Gly Asn Thr Trp Ser
 65                  70                  75                  80

Tyr Phe Asn Lys Asp Leu Lys Leu Lys Ala Gly Asp Val Ile His Tyr
                 85                  90                  95

Trp Val Phe Ile Gln Phe Leu Lys Leu Gly Tyr Arg Lys Asp Asn Gln
            100                 105                 110

Val Trp Asn Val Thr Glu Leu Val Gln Leu Lys Asn Ser Ser Cys Glu
        115                 120                 125

Thr Ser Pro Thr Thr Val Arg Gly Arg Ser Val Ile Cys Lys Asn Ser
    130                 135                 140

Ile Ile Phe Glu Glu Asn Phe Asn Gly Glu Gly Ile Asp Thr Lys Lys
145                 150                 155                 160

Trp Leu Ile Glu Gln Tyr Ile Pro Thr Tyr Thr Ser Leu Asp Tyr Glu
                165                 170                 175

Phe Val Ser Tyr Gln Asn Asp Pro Thr Val Cys Phe Leu Asn Asp Asn
            180                 185                 190

Lys Leu Phe Ile Lys Pro Lys Tyr Ala Gln Ser Glu Ala Glu Val Asn
        195                 200                 205

Gly Glu Leu Asp Phe Arg Asn Arg Cys Thr Arg Lys Thr Asp Glu Glu
    210                 215                 220

Cys Tyr Lys Lys Arg Glu Ile Tyr Phe Ile Ile Pro Pro Val Thr Ser
225                 230                 235                 240
```

```
Gly Arg Leu Val Ser Asp Phe Arg Phe Lys Tyr Gly Lys Val Glu Ile
                245                 250                 255

Arg Ala Lys Leu Pro Ala Gly Asp Trp Ile Tyr Pro Gln Met Tyr Leu
            260                 265                 270

Glu Gln Val Asn Asp Pro Lys Lys Ile Trp Ile Gly Tyr Ala Arg
        275                 280                 285

Gly Asn Asn Lys Leu Leu Ala Asn Asn Gln Glu Asp Ile Gly Gly Asn
        290                 295                 300

Leu Leu Phe Gly Gly Pro Val Leu Asp Pro Glu Glu Pro His Arg Ser
305                 310                 315                 320

Gln Tyr Leu Lys Ser Thr Arg Asn Ser Lys Pro Phe Thr Ser Gln Met
                325                 330                 335

His Thr Leu Val Val Leu Trp Asp Glu Asp His Ile Ser Leu Gln Leu
            340                 345                 350

Asn Gly Ile Glu Tyr Gly Lys Ile Asp Lys Arg Thr Met Gln Glu Val
        355                 360                 365

Asn Phe Ala Asp Asn Asp Met Val Arg Leu Val Leu Gly Val Gly Val
        370                 375                 380

Gly Gly Val Asn Asp Phe Pro Asp Asp Phe Arg Ser Gly Thr Asn Val
385                 390                 395                 400

Lys Pro Trp Arg Asn Lys Asp Asn Lys Gln Val Lys Asn Phe Phe Thr
                405                 410                 415

Ala Arg Ser Glu Trp Gly Lys Thr Trp Ser Gly Asp Asn Cys Ala Leu
            420                 425                 430

Gln Val Asp Tyr Ile Lys Val Trp Ala Leu
        435                 440

<210> SEQ ID NO 3
<211> LENGTH: 1329
<212> TYPE: DNA
<213> ORGANISM: Tenebrio molitor

<400> SEQUENCE: 3
atgtttgcta aagcaataat attgtttctt atattaacca ctttccaatg tcatggagaa      60
tttgttatac cggaagtgac gttagaagcg tacgaaccga aagggtttag agcatcaatt     120
ccagccttaa atggaataca gatgtttgct tttcatggga atataaacaa accaatatcg     180
caggttgatc ctggagagta cagtcaagat tatacttctc caactggtaa tacgtggtct     240
tattttaaca aagacttgaa gctaaaagcc ggggatgtaa ttcattactg gtatttatc     300 caattttaa aattaggata tagaaaagac aatcaagtgt ggaacgtaac agaactggtg     360
cagttaaaaa actcatcctg tgagacaagt cctacaacag ttagaggaag atctgtgatt     420
tgtaaaaata gcattatttt tgaagaaaat ttcaacgggg aaggaattga caccaagaaa     480
tggcttatcg aacaatatat tcccacgtat accagcctgg attatgaatt tgtttcttat     540
caaaatgacc caactgtatg ttttttaaat gacaataaac tatttataaa accaaaatat     600
gcacaaagtg aagccgaagt aaatggtgaa ctagatttta gaaacagatg tactaggaaa     660
acagatgaag aatgttataa aaaacgagaa atttatttca taattccacc tgtgacttct     720
ggaagacttg tttctgattt tcgatttaaa tatggtaaag ttgaaattag ggcgaagtta     780
cctgcagggg actggatata tccacaaatg tacttagaac aagtaaatga tccaaaaaag     840
aaaatatgga ttggttatgc cagaggaaat aataaattac tggcaaataa tcaggaagac     900
attggaggca atttactttt tggtggacct gtttagatc cagaagaacc tcatagaagt     960
caatatttga aaagtactcg gaacagcaaa ccttttacaa gtcaaatgca cactcttgtt    1020
```

```
gtactttggg atgaagatca catttcgtta caattaaatg gtattgaata tggcaagatc    1080
gataaaagga caatgcaaga agtaaacttt gcagataacg atatggtccg cttagttctt    1140
ggagtagggg tgggaggagt caatgatttc ccagatgatt tccgatcagg aactaacgta    1200
aaaccttggc gcaacaaaga caataaacaa gttaaaaatt tctttacggc aagaagtgaa    1260
tgggggaaaa cttggagcgg tgacaattgt gctttacagg ttgattatat taaagtgtgg    1320
gctttatag                                                             1329
```

<210> SEQ ID NO 4
<211> LENGTH: 632
<212> TYPE: PRT
<213> ORGANISM: Tenebrio molitor

<400> SEQUENCE: 4

```
Met Cys Asn Val Arg Thr Leu Leu Gln Val Ile Cys Leu Ser Leu Ile
1               5                   10                  15

Val Ile Gln Thr Val Asp Ser Tyr Ser Phe Ala Leu Ser Lys Phe Thr
            20                  25                  30

Arg Ile Arg Arg Gln Ala Arg Arg Thr Cys Thr Ser Thr Glu Phe Ala
        35                  40                  45

Cys Lys Ser Gly Glu Cys Ile Asp Glu Asp Lys Glu Cys Asp Gly Ile
    50                  55                  60

Val Asp Cys Thr Asp Ala Ser Asp Glu Thr Asn Ala Cys His Arg Ile
65                  70                  75                  80

Lys Cys Pro Asn Tyr Leu Phe Arg Cys Lys Tyr Gly Ala Cys Ile Asn
                85                  90                  95

Pro Asp Leu Glu Cys Asp Gly Lys Pro Asp Cys Met Asp Gly Ser Asp
            100                 105                 110

Glu Lys Thr Ser Lys Cys Lys Pro Asp Ser Ser Pro Glu Cys Lys
        115                 120                 125

Ala Asn Glu Phe Arg Cys Ser Ser Gly Gln Cys Ile Pro Glu Asp Phe
    130                 135                 140

Lys Cys Asp Gly Lys Ala Glu Cys Lys Asp Asn Ser Asp Glu Ile Arg
145                 150                 155                 160

Ala Thr Cys Trp Asn Val Arg Cys Pro Gly Phe Thr His Lys Cys Lys
                165                 170                 175

Tyr Gly Ala Cys Val Ser Gly Asn Ala Glu Cys Asn Gly Ile Val Glu
            180                 185                 190

Cys Phe Asp Gly Ser Asp Glu Asp Pro Ala Ile Cys Lys Thr Lys Pro
        195                 200                 205

Thr Pro Arg Pro Thr Pro Thr Pro Gly Thr Pro Gly Pro Gln Pro Thr
    210                 215                 220

Gln Gly Gly Cys Val Leu Pro Asn His Pro Glu Phe Gly Glu Trp Gln
225                 230                 235                 240

Val Tyr Gly Ile Pro Gly Gln Phe Ser Pro Gly Met Val Ile Arg Ala
                245                 250                 255

Gly Ala Thr Leu Arg Ile Gln Cys Lys Lys Arg Tyr Lys Leu Glu Gly
            260                 265                 270

Lys Asn Ala Ile Phe Cys Glu Asn Gly Lys Trp Ser Asp Ala Val Gly
        275                 280                 285

His Cys Leu Lys Leu Cys Pro Ser Ile Gln Ser Thr Ser Thr Met Arg
    290                 295                 300

Val Thr Cys Ile Tyr Asn Lys His Glu Glu Thr Glu Asn Cys Thr Glu
305                 310                 315                 320
```

Ala Val Glu Gly Thr Leu Val Arg Phe Asp Cys Ala Pro Phe Tyr Glu
            325                 330                 335

Asp Leu Gly Leu Ser Arg His Pro Ile His Ile Cys Arg Asp Gly Ser
            340                 345                 350

Trp Asp Gln Arg Arg Pro Glu Cys Thr Pro Val Cys Gly Gln Lys Ser
            355                 360                 365

Val Asn Ala Gln Thr Leu Ile Val Asn Gly Lys Pro Val Lys Lys Gly
            370                 375                 380

Asp Tyr Pro Trp Gln Val Ala Leu Tyr Thr Leu Asn Asp Lys Glu Leu
385                 390                 395                 400

Ile Cys Gly Gly Ser Leu Leu Asn Gln Arg Val Leu Thr Ala Ala
            405                 410                 415

His Cys Ile Thr Asp Asp Lys Gly Lys Leu Leu Ser Lys Glu Asn Tyr
            420                 425                 430

Met Val Ala Val Gly Lys Tyr Tyr Arg Pro Phe Asn Asp Ser Arg Asp
            435                 440                 445

Arg Asn Glu Ala Gln Phe Ser Glu Val Lys His Met Phe Ile Pro Glu
    450                 455                 460

Leu Tyr Lys Gly Ser Thr Gln Asn Tyr Val Gly Asp Ile Ala Ile Leu
465                 470                 475                 480

Val Thr Arg Val Thr Phe Thr Leu Ser Arg Arg Val Gln Pro Val Cys
            485                 490                 495

Ile Asp Tyr Gly Leu Lys Tyr Thr Ser Tyr Thr Asn Glu Phe Gly Tyr
            500                 505                 510

Val Thr Gly Trp Gly Tyr Thr Leu Gln Asn Asp Lys Pro Ser Asp Val
            515                 520                 525

Leu Lys Glu Leu Lys Val Pro Ala Val Ser Thr Glu Gln Cys Ser Ser
    530                 535                 540

Ala Ile Pro Glu Asp Tyr Asp Ile Tyr Leu Thr His Asp Lys Leu Cys
545                 550                 555                 560

Ala Gly Tyr Leu Asp Asn Gly Thr Ser Val Cys Ser Gly Asp Ser Gly
            565                 570                 575

Gly Gly Leu Val Phe Lys Phe Asp Gly Arg Tyr Tyr Val Thr Gly Ile
            580                 585                 590

Val Ser Leu Ser Pro Gln Ala Ser Thr Gly Gly Cys Asp Thr Gln Gln
            595                 600                 605

Tyr Gly Leu Tyr Thr Lys Val Gly Thr Tyr Ile Ser Asp Phe Ile Ile
            610                 615                 620

Lys Thr Glu Ser Gln Phe Arg Pro
625                 630

<210> SEQ ID NO 5
<211> LENGTH: 1899
<212> TYPE: DNA
<213> ORGANISM: Tenebrio molitor

<400> SEQUENCE: 5
atgtgcaatg taagaacatt actgcaggtg atttgtttaa gtcttattgt tatacagaca      60
gtcgatagct acagttttgc actaagcaaa tttacgagaa ttcgacgcca agcccgacga     120
acctgtacaa gtactgagtt tgcttgcaaa tccggagaat gcatcgacga agataaagag     180
tgtgacggta ttgtggactg tacagatgcc agcgacgaga ccaacgcctg tcacaggatc     240
aaatgcccca attatctgtt ccggtgcaaa tatggcgctt gcatcaatcc ggacctggag     300
tgcgacggca aaccggactg catggacgga tccgacgaga aaacgtcgaa atgtaaaccc     360

```
gacgattcgt ccccggagtg caaagcgaac gagtttcggt gcagctccgg tcagtgcatc    420
ccggaggact tcaaatgtga cggcaaagcc gagtgcaagg ataactccga cgagattaga    480
gccacctgct ggaacgtccg ctgtccagga ttcacgcaca agtgcaaata cggagcttgc    540
gtgagcggta acgccgagtg caacggaatc gtcgagtgtt tcgacggttc agacgaagat    600
ccggcgattt gcaaaactaa accgacacca aggccgacgc cgactccagg aactcccggc    660
ccgcaaccga cacagggtgg ctgcgtcttg ccgaatcatc ccgaatttgg tgagtggcaa    720
gtgtacggaa ttcctggaca attctctcca ggaatggtga ttagagctgg tgcaactttg    780
cgaatacagt gcaagaaacg ttacaaactc gaaggaaaaa acgccatctt ttgcgaaaat    840
gggaagtggt cggatgcagt cggtcattgc ttaaagttgt gcccttccat ccaaagtact    900
tcaacaatga gggttacttg tatttataac aaacacgaag agactgaaaa ctgcacagaa    960
gctgttgagg gtactcttgt gaggtttgat tgcgcaccgt tttatgaaga tttgggattg   1020
tcgagacatc ctattcatat ctgccagat ggttcctggg accagaggag accagaatgt   1080
acaccagtgt gtgggcaaaa gtcagttaac gctcaaacat taattgtcaa cgggaaaccc   1140
gtgaagaaag gagattatcc gtggcaagtc gcgttataca ctttgaacga taaagagttg   1200
atctgtggag gatccctctt aaaccagcga gtcgttctga cagctgcgca ttgtataact   1260
gacgataagg gaaaattgtt atcaaaggaa aattatatgg tggctgtggg aaagtactac   1320
cgaccattca atgactctcg agaccgcaac gaagcccagt tttctgaggt aaaacacatg   1380
tttattcccg aactgtacaa gggttccaca caaaactacg tcggagatat cgctatcttg   1440
gtaacacgag tcactttcac cctttccagg agagttcagc cggtgtgcat cgactacggt   1500
ttaaaataca cctcttatac aaacgaattt ggatacgtta cgggttgggg ttacactctg   1560
caaaatgaca aaccttccga cgtgctcaaa gaattgaaag ttccagcagt tagtacagaa   1620
caatgtagta cgctattcc tgaagattat gacatctacc ttacacacga taaactgtgc   1680
gccggctatt tagacaatgg tacttccgtg tgtagcggag acagtggtgg aggtttggtg   1740
tttaaatttg atggcaggta ctacgttact gggattgtga gtctttctcc acaagcatca   1800
acaggcggct gtgatactca acaatatggt ctttatacaa aggttggcac ctacatttcg   1860
gattttatta tcaaaacgga atcgcagttt aggccataa                          1899
```

<210> SEQ ID NO 6
<211> LENGTH: 632
<212> TYPE: PRT
<213> ORGANISM: Tenebrio molitor

<400> SEQUENCE: 6

```
Met Cys Asn Val Arg Thr Leu Leu Gln Val Ile Cys Leu Ser Leu Ile
1               5                   10                  15

Val Ile Gln Thr Val Asp Ser Tyr Ser Phe Ala Leu Ser Lys Phe Thr
            20                  25                  30

Arg Ile Arg Arg Pro Ala Arg Arg Thr Cys Thr Ser Thr Glu Phe Ala
        35                  40                  45

Cys Lys Ser Gly Glu Cys Ile Asp Glu Asp Lys Glu Cys Asp Gly Ile
    50                  55                  60

Val Asp Cys Thr Asp Ala Ser Asp Glu Thr Asn Ala Cys His Arg Ile
65                  70                  75                  80

Lys Cys Pro Asn Tyr Leu Phe Arg Cys Lys Tyr Gly Ala Cys Ile Asn
                85                  90                  95

Pro Asp Leu Glu Cys Asp Gly Lys Pro Asp Cys Met Asp Gly Ser Asp
```

```
                100                 105                 110
Glu Lys Ala Ser Lys Cys Lys Pro Asp Asp Ser Ser Pro Glu Cys Lys
            115                 120                 125

Ala Asn Glu Phe Arg Cys Ser Ser Gly Gln Cys Ile Pro Glu Asp Tyr
130                 135                 140

Lys Cys Asp Gly Lys Ala Glu Cys Lys Asp Asn Ser Asp Glu Ile Arg
145                 150                 155                 160

Ala Thr Cys Trp Asn Val Arg Cys Pro Gly Phe Thr His Lys Cys Lys
                165                 170                 175

Tyr Gly Ala Cys Val Ser Gly Asn Ala Glu Cys Asn Gly Ile Val Glu
            180                 185                 190

Cys Phe Asp Gly Ser Asp Glu Asp Pro Ala Ile Cys Lys Thr Glu Pro
        195                 200                 205

Thr Pro Lys Pro Thr Pro Thr Pro Gly Thr Pro Gly Pro Gln Pro Thr
    210                 215                 220

Gln Gly Gly Cys Val Leu Pro Asn His Pro Glu Phe Gly Glu Trp Gln
225                 230                 235                 240

Val Tyr Gly Ile Pro Gly Gln Phe Ser Pro Gly Met Ala Ile Arg Ala
                245                 250                 255

Gly Ala Thr Leu Arg Ile Gln Cys Lys Lys Arg Tyr Lys Leu Glu Gly
            260                 265                 270

Lys Asn Ala Ile Phe Cys Glu Asn Gly Lys Trp Ser Asp Ala Val Gly
        275                 280                 285

His Cys Leu Lys Leu Cys Pro Ser Ile Gln Ser Thr Ser Thr Met Arg
    290                 295                 300

Val Thr Cys Ile Tyr Asn Lys His Glu Glu Thr Glu Asn Cys Thr Glu
305                 310                 315                 320

Ala Val Glu Gly Thr Leu Val Arg Phe Asp Cys Ala Pro Phe Tyr Glu
                325                 330                 335

Asp Leu Gly Leu Ser Arg His Pro Ile His Ile Cys Arg Asp Gly Ser
            340                 345                 350

Trp Asp Gln Arg Arg Pro Glu Cys Thr Pro Val Cys Gly Gln Lys Ser
        355                 360                 365

Val Asn Ala Gln Thr Leu Ile Val Asn Gly Lys Pro Val Lys Lys Gly
    370                 375                 380

Asp Tyr Pro Trp Gln Val Ala Leu Tyr Thr Leu Asn Asp Lys Glu Leu
385                 390                 395                 400

Ile Cys Gly Gly Ser Leu Leu Asn Gln Arg Val Val Leu Thr Ala Ala
                405                 410                 415

His Cys Ile Thr Asp Asp Lys Gly Lys Leu Leu Ser Lys Glu Asn Tyr
            420                 425                 430

Met Val Ala Val Gly Lys Tyr Tyr Arg Pro Phe Asn Asp Ser Arg Asp
        435                 440                 445

Arg Asn Glu Ala Gln Phe Ser Glu Val Lys His Met Phe Ile Pro Glu
    450                 455                 460

Leu Tyr Lys Gly Ser Thr Gln Asn Tyr Val Gly Asp Ile Ala Ile Leu
465                 470                 475                 480

Val Thr Arg Val Thr Phe Thr Leu Ser Arg Arg Val Gln Pro Val Cys
                485                 490                 495

Ile Asp Tyr Gly Leu Lys Tyr Thr Ser Tyr Thr Asn Glu Phe Gly Tyr
            500                 505                 510

Val Thr Gly Trp Gly Tyr Thr Leu Gln Asn Asp Lys Pro Ser Asp Val
        515                 520                 525
```

-continued

| Leu | Lys | Glu | Leu | Lys | Val | Pro | Ala | Val | Ser | Thr | Glu | Gln | Cys | Ser | Ser |
|     |     |     |     | 530 |     |     |     | 535 |     |     |     | 540 |     |     |     |

| Ala | Ile | Pro | Glu | Asp | Tyr | Asp | Ile | Tyr | Leu | Thr | His | Asp | Lys | Leu | Cys |
| 545 |     |     |     |     | 550 |     |     |     |     | 555 |     |     |     |     | 560 |

| Ala | Gly | Tyr | Leu | Asp | Asn | Gly | Thr | Ser | Val | Cys | Ser | Gly | Asp | Ser | Gly |
|     |     |     |     | 565 |     |     |     |     | 570 |     |     |     |     | 575 |     |

| Gly | Gly | Leu | Val | Phe | Lys | Phe | Asp | Gly | Arg | Tyr | Tyr | Val | Thr | Gly | Ile |
|     |     |     |     | 580 |     |     |     |     | 585 |     |     |     |     | 590 |     |

| Val | Ser | Leu | Ser | Pro | Gln | Ala | Ser | Thr | Gly | Gly | Cys | Asp | Thr | Gln | Gln |
|     |     |     |     | 595 |     |     |     |     | 600 |     |     |     |     | 605 |     |

| Tyr | Gly | Leu | Tyr | Thr | Lys | Val | Gly | Thr | Tyr | Ile | Ser | Asp | Phe | Ile | Ile |
|     |     |     |     | 610 |     |     |     |     | 615 |     |     |     |     | 620 |     |

| Lys | Thr | Glu | Ser | Gln | Phe | Arg | Pro |
| 625 |     |     |     |     | 630 |     |     |

<210> SEQ ID NO 7
<211> LENGTH: 1899
<212> TYPE: DNA
<213> ORGANISM: Tenebrio molitor

<400> SEQUENCE: 7

```
atgtgcaatg taagaacatt actgcaggtg atttgtttaa gtcttattgt tatacagaca       60
gtcgatagct acagttttgc actaagcaaa tttacgagaa ttcgacgccc agcccgacga      120
acctgtacaa gtactgagtt tgcttgcaaa tccggagaat gcatcgacga agataaagag      180
tgtgacggta ttgtagactg tacagatgcc agcgacgaga ccaacgcctg tcacaggatc      240
aaatgcccca attatctgtt ccggtgcaaa tatggcgctt gcatcaatcc ggacctggag      300
tgcgacggca aaccggactg catggacgga tccgacgaga aagcgtcgaa atgtaaaccc      360
gacgattcgt ccccggagtg caaagcgaac gagtttcggt gcagctccgg tcagtgcatc      420
ccggaggact acaaatgcga cggcaaagcc gagtgcaagg ataactccga cgagattaga      480
gccacctgct ggaacgtccg ctgtccagga ttcacgcaca agtgcaaata cggagcttgc      540
gtgagcggta acgccgagtg caacggaatc gtcgagtgtt tcgacggttc agacgaagat      600
ccggcgattt gcaagactga accgacacca aaaccgacgc cgactccagg aactcccggc      660
ccgcaaccga cacagggtgg ctgcgtcttg ccgaatcatc ccgaatttgg tgagtggcaa      720
gtgtacggaa ttcctggaca attctctcca ggaatggcga ttagagctgg tgcaactttg      780
cgaatacagt gcaagaaacg ttacaaactc gaaggaaaaa acgccatctt ttgcgaaaat      840
gggaagtggt cggatgcagt cggtcattgc ttaaagttgt gcccttccat ccaaagtact      900
tcaacaatga gggttacttg tatttataac aaacacgaag agactgaaaa ctgcacagaa      960
gctgttgagg gtactcttgt gaggtttgat tgcgcaccgt tttatgaaga tttgggattg     1020
tcgagacatc ctattcatat ctgccgagat ggttcctggg accagaggag accagaatgt     1080
acaccagtgt gtgggcaaaa gtcagttaac gctcaaacat taattgtcaa cgggaaaccc     1140
gtgaagaaag gagattatcc atggcaagtc gcgttataca ctttgaacga taaagagttg     1200
atctgtggag gatccctctt aaaccagcga gtcgttctga cagctgcgca ttgtataact     1260
gacgataagg gaaaattgtt atcaaaggaa aattatatgg tggctgtggg aaagtactac     1320
cgaccattca atgactctcg agaccgcaac gaagcccagt tttccgaggt aaaacacatg     1380
tttattccag aactgtacaa gggttccaca caaaactacg tcggagatat cgctatcttg     1440
gtaacacgag tcactttcac cctttccagg agagttcagc cggtgtgcat cgactacggt     1500
ttaaaataca cctcttatac aaacgaattt ggatacgtta cgggttgggg ttacactctg     1560
```

```
caaaatgaca aaccttccga cgtgctcaaa gaattgaaag ttccagcagt tagtacagaa    1620
caatgtagta gcgctatacc tgaagattat gacatctacc ttacacacga taaactgtgc    1680
gctggctatt tagacaatgg tacttccgtg tgtagcggag acagtggtgg aggtttggtg    1740
tttaaatttg atggcaggta ctacgttact gggattgtga gtctttctcc acaagcatca    1800
acaggcggct gtgatactca acaatatggt ctttatacaa aggttggcac ctacatttcg    1860
gattttatta tcaaaacgga atcgcagttt aggccataa                           1899

<210> SEQ ID NO 8
<211> LENGTH: 20
<212> TYPE: DNA
<213> ORGANISM: Tenebrio molitor
<220> FEATURE:
<221> NAME/KEY: misc_feature
<222> LOCATION: (1)..(20)
<223> OTHER INFORMATION: Degenerate sense forward primer

<400> SEQUENCE: 8
gargcntayg arccnaargg                                                  20

<210> SEQ ID NO 9
<211> LENGTH: 20
<212> TYPE: DNA
<213> ORGANISM: Tenebrio molitor
<220> FEATURE:
<221> NAME/KEY: misc_feature
<222> LOCATION: (1)..(20)
<223> OTHER INFORMATION: Degenerate antisense reverse primer

<400> SEQUENCE: 9
atrtcytcyt grttrttngc                                                  20

<210> SEQ ID NO 10
<211> LENGTH: 20
<212> TYPE: DNA
<213> ORGANISM: Tenebrio molitor
<220> FEATURE:
<221> NAME/KEY: misc_feature
<222> LOCATION: (1)..(20)
<223> OTHER INFORMATION: Degenerate sense forward primer

<400> SEQUENCE: 10
aargayaayt gygaygarat                                                  20

<210> SEQ ID NO 11
<211> LENGTH: 20
<212> TYPE: DNA
<213> ORGANISM: Tenebrio molitor
<220> FEATURE:
<221> NAME/KEY: misc_feature
<222> LOCATION: (1)..(20)
<223> OTHER INFORMATION: Degenerate antisense reverse primer

<400> SEQUENCE: 11
gcytgytgcc anggrtartc                                                  20

<210> SEQ ID NO 12
<211> LENGTH: 30
<212> TYPE: PRT
<213> ORGANISM: Tenebrio molitor
<220> FEATURE:
<221> NAME/KEY: MISC_FEATURE
<222> LOCATION: (1)..(30)
<223> OTHER INFORMATION: band 1 in FIG. 11(A)

<400> SEQUENCE: 12
```

```
Glu Phe Val Ile Pro Glu Val Thr Leu Glu Ala Tyr Glu Pro Lys Gly
1               5                   10                  15

Phe Arg Ala Ser Ile Pro Ala Leu Asn Gly Ile Gln Met Phe
            20                  25                  30

<210> SEQ ID NO 13
<211> LENGTH: 30
<212> TYPE: PRT
<213> ORGANISM: Tribolium castaneum
<220> FEATURE:
<221> NAME/KEY: MISC_FEATURE
<222> LOCATION: (1)..(30)
<223> OTHER INFORMATION: Tc-GNBP in FIG. 11(A)

<400> SEQUENCE: 13

Gln Phe Val Ile Pro Asp Val Thr Leu Glu Ala Tyr Ala Pro Lys Gly
1               5                   10                  15

Phe Arg Ala Ser Ile Pro Ala Leu Pro Gly Ile Gln Met Phe
            20                  25                  30

<210> SEQ ID NO 14
<211> LENGTH: 30
<212> TYPE: PRT
<213> ORGANISM: Tenebrio molitor
<220> FEATURE:
<221> NAME/KEY: MISC_FEATURE
<222> LOCATION: (1)..(30)
<223> OTHER INFORMATION: Tm-GRP in FIG. 11(A)

<400> SEQUENCE: 14

Gln Phe Glu Val Pro Asp Ala Leu Val Glu Val Phe Arg Pro Arg Gly
1               5                   10                  15

Leu Arg Val Ser Ile Pro Asp Gln Glu Gly Ile Lys Leu Phe
            20                  25                  30

<210> SEQ ID NO 15
<211> LENGTH: 30
<212> TYPE: PRT
<213> ORGANISM: Anopheles gambiae
<220> FEATURE:
<221> NAME/KEY: MISC_FEATURE
<222> LOCATION: (1)..(30)
<223> OTHER INFORMATION: Ag-GNBP1 in FIG. 11(A)

<400> SEQUENCE: 15

Ala Tyr Thr Ile Pro Ala Val Arg Phe Glu Tyr Pro Thr Met Arg Gly
1               5                   10                  15

Phe Arg Ala Ser Ile Pro Asp Thr Pro Gly Leu Gln Met Phe
            20                  25                  30

<210> SEQ ID NO 16
<211> LENGTH: 29
<212> TYPE: PRT
<213> ORGANISM: Drosophila melanogaster
<220> FEATURE:
<221> NAME/KEY: MISC_FEATURE
<222> LOCATION: (1)..(29)
<223> OTHER INFORMATION: Dm-GNBP1 in FIG. 11(A)

<400> SEQUENCE: 16

Ala Tyr Lys Ile Pro Thr Pro Thr Val Glu Leu Leu Glu Thr Gly Phe
1               5                   10                  15

Ser Val Ser Ile Pro Asp Glu Glu Gly Val Lys Val Val
            20                  25
```

-continued

```
<210> SEQ ID NO 17
<211> LENGTH: 20
<212> TYPE: PRT
<213> ORGANISM: Tenebrio molitor
<220> FEATURE:
<221> NAME/KEY: MISC_FEATURE
<222> LOCATION: (1)..(20)
<223> OTHER INFORMATION: band 2 in FIG. 11(B)

<400> SEQUENCE: 17

Ile Val Asn Gly Lys Pro Val Lys Lys Gly Asp Tyr Pro Trp Gln Gln
1               5                   10                  15

Ala Leu Tyr Thr
            20

<210> SEQ ID NO 18
<211> LENGTH: 20
<212> TYPE: PRT
<213> ORGANISM: Tribolium castaneum
<220> FEATURE:
<221> NAME/KEY: MISC_FEATURE
<222> LOCATION: (1)..(20)
<223> OTHER INFORMATION: Tc-SP in FIG. 11(B)

<400> SEQUENCE: 18

Ile Val Asn Gly Lys Thr Ala Lys Arg Gly Thr Tyr Pro Trp Gln Ala
1               5                   10                  15

Ala Leu Tyr Thr
            20

<210> SEQ ID NO 19
<211> LENGTH: 20
<212> TYPE: PRT
<213> ORGANISM: Manduca sexta
<220> FEATURE:
<221> NAME/KEY: MISC_FEATURE
<222> LOCATION: (1)..(20)
<223> OTHER INFORMATION: Ms-HP14 in FIG. 11(B)

<400> SEQUENCE: 19

Val Leu Gly Gly Glu Arg Ala Gln Phe Gly Glu Leu Pro Trp Gln Ala
1               5                   10                  15

Gly Ile Tyr Thr
            20

<210> SEQ ID NO 20
<211> LENGTH: 20
<212> TYPE: PRT
<213> ORGANISM: Anopheles gambiae
<220> FEATURE:
<221> NAME/KEY: MISC_FEATURE
<222> LOCATION: (1)..(20)
<223> OTHER INFORMATION: Ag-SP in FIG. 11(B)

<400> SEQUENCE: 20

Ile Ile Gly Gly Arg Asn Val Ser Ile Ala Glu Val Pro Trp His Met
1               5                   10                  15

Ala Ile Tyr Lys
            20

<210> SEQ ID NO 21
<211> LENGTH: 14
<212> TYPE: PRT
<213> ORGANISM: Drosophila melanogaster
<220> FEATURE:
<221> NAME/KEY: MISC_FEATURE
<222> LOCATION: (1)..(14)
<223> OTHER INFORMATION: Dm-SP in FIG. 11(B)
```

```
<400> SEQUENCE: 21

Ile Asn Asn Thr Val Val Pro Trp His Val Gly Leu Tyr Val
1               5                   10

<210> SEQ ID NO 22
<211> LENGTH: 21
<212> TYPE: PRT
<213> ORGANISM: Tenebrio molitor
<220> FEATURE:
<221> NAME/KEY: MISC_FEATURE
<222> LOCATION: (1)..(21)
<223> OTHER INFORMATION: Peak 1 in FIG. 11(C)

<400> SEQUENCE: 22

Asp Asn Ser Asp Glu Ile Arg Ala Thr Cys Trp Asn Val Arg Cys Pro
1               5                   10                  15

Gly Phe Thr His Lys
            20

<210> SEQ ID NO 23
<211> LENGTH: 21
<212> TYPE: PRT
<213> ORGANISM: Tribolium castaneum
<220> FEATURE:
<221> NAME/KEY: MISC_FEATURE
<222> LOCATION: (1)..(21)
<223> OTHER INFORMATION: Tc-SP 149-170 in FIG.11(C)

<400> SEQUENCE: 23

Asp Arg Ser Asp Glu Ile Arg Ala Thr Cys Trp Asn Leu Arg Cys Pro
1               5                   10                  15

Ile Tyr Ser Tyr Lys
            20

<210> SEQ ID NO 24
<211> LENGTH: 14
<212> TYPE: PRT
<213> ORGANISM: Tenebrio molitor
<220> FEATURE:
<221> NAME/KEY: MISC_FEATURE
<222> LOCATION: (1)..(14)
<223> OTHER INFORMATION: Peak 2 in FIG. 11(C)

<400> SEQUENCE: 24

Tyr Gly Ala Cys Ile Asn Ile Ala Leu Glu Cys Asp Pro Lys
1               5                   10

<210> SEQ ID NO 25
<211> LENGTH: 14
<212> TYPE: PRT
<213> ORGANISM: Tribolium castaneum
<220> FEATURE:
<221> NAME/KEY: MISC_FEATURE
<222> LOCATION: (1)..(14)
<223> OTHER INFORMATION: Tc-SP 86-99 in FIG.11(C)

<400> SEQUENCE: 25

Tyr Gly Ala Cys Ile Ser Ala Asp Leu Glu Cys Asp Gly Lys
1               5                   10
```